(12) United States Patent
Jiang et al.

(10) Patent No.: US 9,782,381 B2
(45) Date of Patent: Oct. 10, 2017

(54) MOLECULAR TARGETS FOR HEALING OR TREATING WOUNDS

(71) Applicant: UNIVERSITY COLLEGE CARDIFF CONSULTANTS LIMITED, Cardiff, South Glamorgan (GB)

(72) Inventors: Wenguo Jiang, South Glamorgan (GB); Keith Harding, South Glamorgan (GB)

(73) Assignee: University College Cardiff Consultants Limited, Cardiff (GB)

( * ) Notice: Subject to any disclaimer, the term of this patent is extended or adjusted under 35 U.S.C. 154(b) by 0 days.

(21) Appl. No.: 15/149,638

(22) Filed: May 9, 2016

(65) Prior Publication Data

US 2016/0331716 A1 Nov. 17, 2016

Related U.S. Application Data

(62) Division of application No. 14/000,532, filed as application No. PCT/GB2012/050362 on Feb. 17, 2012, now abandoned.

(51) Int. Cl.

| | | |
|---|---|---|
| C12N 15/11 | (2006.01) |
| A61K 31/29 | (2006.01) |
| C12N 15/113 | (2010.01) |
| A61K 9/00 | (2006.01) |
| A61K 45/06 | (2006.01) |
| A61K 9/06 | (2006.01) |
| A61K 31/555 | (2006.01) |
| A61K 31/713 | (2006.01) |

(52) U.S. Cl.
CPC ............ *A61K 31/29* (2013.01); *A61K 9/0014* (2013.01); *A61K 9/0019* (2013.01); *A61K 9/06* (2013.01); *A61K 31/555* (2013.01); *A61K 31/713* (2013.01); *A61K 45/06* (2013.01); *C12N 15/1138* (2013.01); *C12N 2310/11* (2013.01); *C12N 2310/121* (2013.01); *C12N 2310/14* (2013.01); *C12N 2320/30* (2013.01); *C12N 2320/31* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 2004/0009597 A1 | 1/2004 | Cowsert et al. | |
| 2005/0170445 A1 | 8/2005 | Reichert et al. | |
| 2006/0165761 A1* | 7/2006 | Trotter | A61L 15/20 424/445 |
| 2006/0275770 A1 | 12/2006 | Bednarik | |
| 2009/0028823 A1 | 1/2009 | Yi | |

FOREIGN PATENT DOCUMENTS

| | | |
|---|---|---|
| CN | 101671729 A | 3/2010 |
| WO | 9634117 A1 | 10/1996 |
| WO | 0162276 A | 8/2001 |
| WO | 03075494 A1 | 9/2003 |
| WO | 2004005312 A1 | 1/2004 |
| WO | 2004050894 A2 | 6/2004 |
| WO | 2004070002 A2 | 8/2004 |
| WO | 2005028681 A1 | 3/2005 |
| WO | 2006053162 A1 | 5/2006 |
| WO | 2006108225 A1 | 10/2006 |
| WO | 2007130423 A2 | 11/2007 |
| WO | 2008005276 A2 | 1/2008 |
| WO | 2009076229 A2 | 6/2009 |
| WO | 2010065995 A1 | 6/2010 |
| WO | 2010085606 A1 | 7/2010 |
| WO | 2011033249 A1 | 3/2011 |

OTHER PUBLICATIONS

Affymetrix. Human Genome U133A Array Annotation data, 2009.
Affymetrix. Human Genome U133B Array Annotation data, 2009.
Almeida, et al.; "Randomized, double-blind study of stibogluconate plus human granulocyte macrophage colony-stimulating factor versus stibogluconate alone in the treatment of cutaneous Leishmaniasis"; The Journal of Infectious Diseases, vol. 180, No. 5, pp. 1735-1737 (Oct. 8, 1999).
Burchert, et al.; "CD82 (KAI1), a member of the tetrasoan family, is expressed on early haemopoietic progenitor cells and up-regulated in distinct human leukaemias", Bri. J Haematology, 107:494-504 (1999).
Cooper et al.; "Wound healing and inflammation genes revealed by array analysis of macrophageless\ PU.I null mice", Genome Biol., 6:R5.1-R5.10 (2004).
Derrick, et al.; "Comparitive analysis of global gene expression profiles between diabetic rat wounds treated with vacuum-assisted closure therapy, moist wound healing or gauze under suction"; International Wound Journal, vol. 5, No. 5, pp. 615-624, (Dec. 2008).
GeneCards® CAR1; http://www.genecards.org/index.php?path=/Search/keyword/car1, accessed on Jun. 10, 2013.
Martinez, et al.; "Treatment of Cutaneous Leishmaniasis with Allopurinol and Stibogluconate"; Clinical Infectious Diseases, vol. 24, No. 2, pp. 165-169 (Feb. 1, 1997).
Moseley et al.; "Extracellular matrix metabolites as potential biomarkers of disease activity in wound fluid: lessons learned from other inflammatory diseases?"; British Journal of Dermatology vol. 150, No. 3, pp. 401-413 (Mar. 1, 2004).
Solomon et al.; "Treatment of cutaneous leishmaniasis with intralesional sodium stibogluconate"; Journal of the European Academy of Dermatology and Venereology, vol. 23, No. 10, pp. 1189-1192, (Oct. 1, 2009).
Vandesompele et al.; "Accurate normalization of real-time quantitative RT-PCR data by geometric averging of multiple internal control genes"; Genome Biology 2002; 3(7):0034.1-0034.11.

(Continued)

*Primary Examiner* — Kate Poliakova-Georgantas

(74) *Attorney, Agent, or Firm* — King & Schickli, PLLC

(57) ABSTRACT

Molecular target for healing or treating wounds and, in particular chronic, human wounds, are described. The molecular target is PTPRK, or a protein 50% homologous therewith, and which retains the same activity as PTPRK protein. Further, methods and novel therapeutics are described for treating said wounds.

11 Claims, 22 Drawing Sheets

(56) References Cited

OTHER PUBLICATIONS

Xu, et al.; "Receptor-type Protein-tyrosine Phosphatase-k Regulates Epidermal Growth Factor Receptor Function"; Journal of Biological Chemistry, vol. 280, No. 52, pp. 42694-42700 (Jan. 1, 2005).
International Search Report and Written Opinion for International Application No. PCT/GB2010/001696 dated Nov. 5, 2010.
International Search Report and Written Opinion for International Application No. PCT/GB2010/050362 dated May 24, 2012.
Search Report for British Application No. GB1103898.1 dated Jul. 7, 2011.
Wang, et al.; "Transforming Growth Factor β (TGF-β)—Smad Target Gene Protein Tyrosine Phosphatase Receptor Type Kappa Is Required for TGF-β Function"; Moleclar and Cellular Biology, Jun. 2005, vol. 25, No. 11, pp. 4703-4715.
Hardiman, et al.; "Microarray platforms—comparisons and contrasts"; Pharmacogenomics (2004), vol. 5, No. 5, pp. 487-502.
Larjava, H., et al., Expression of Integrins and Basement Membrane Components by Wound Keratinocytes, 1993, J. Clin. Invest., 92, 3: 1425-1435.
Final Office Action for U.S. Appl. No. 13/326,153 dated Mar. 7, 2014.
Machine Translation of CN 101671729; obtained Feb. 4, 2014; pp. 1-7.

\* cited by examiner

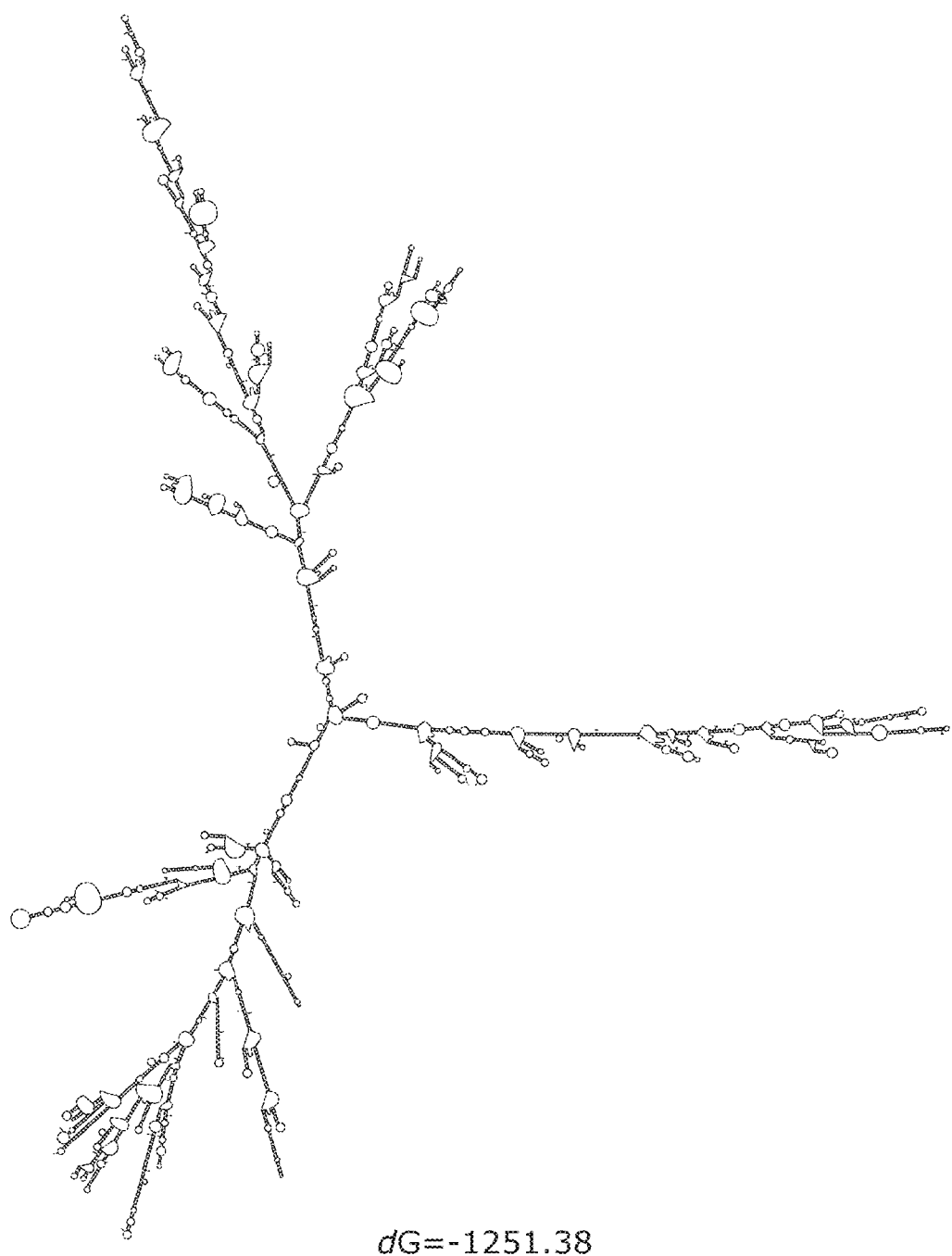
Figure 1 Secondary structure of human PTPRK mRNA

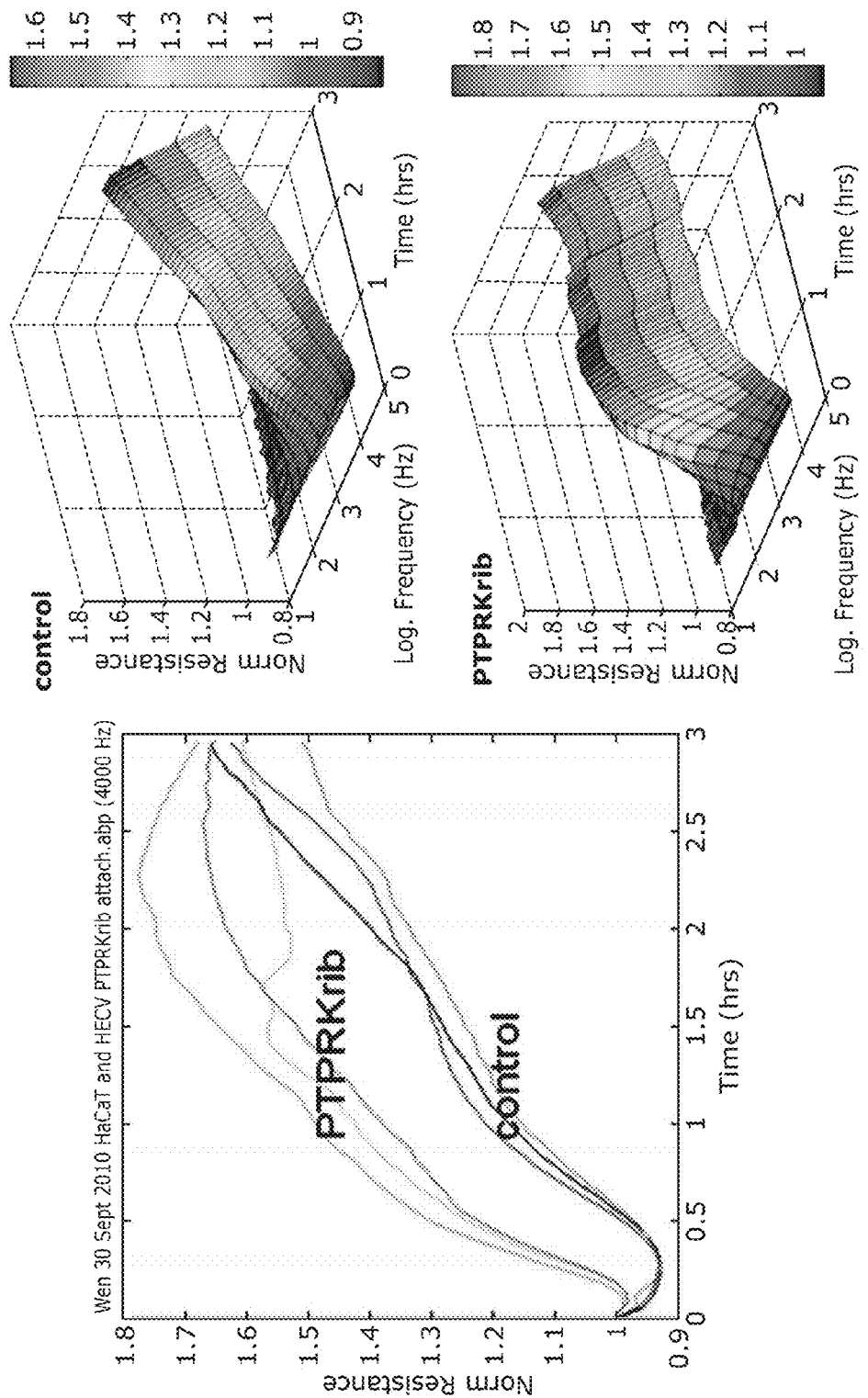
Figure 2A *HaCaT cells after lost PTPRK by way of anti-PTPRK transgenes showed an increase in cell adhesion. Shown are traces at 4000Hz and 3D modeling at 4,000Hz and 500Hz.*

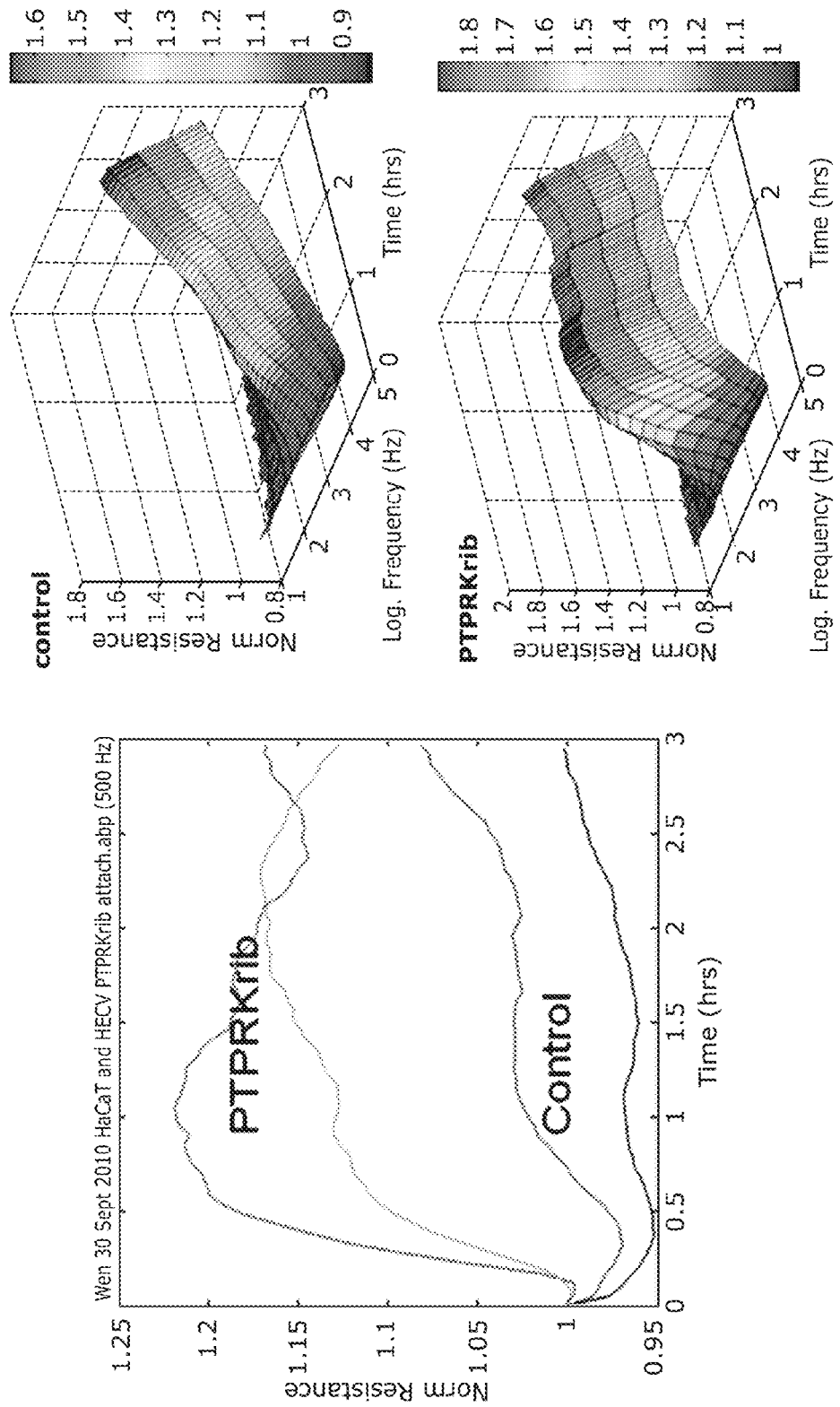
Figure 2B *HaCaT cells after lost PTPRK by way of anti-PTPRK transgenes showed an increase in cell adhesion. Shown are traces at 32,000 Hz and 3D modelling at 4,000Hz and 500Hz.*

Effects of knocking down PTPRK in endothelial cells on the adhesion of the cells and their response to PTPRK inhibitor, stibogluconate. Left: traces of cells response in ECIS assays. Right: A: HECV WT; B: HECV/PTPRKrib; C: HECV wt plus stibogluconate; and D: HECV/PTPRKrib plus stibogluconate.

*Effects of knocking down PTPRK in endothelial cells on cellular migration s and their response to PTPRK inhibitor, stibogluconate. Left: traces of cells response in ECIS assays. Right: A: HECV WT; B: HECV/PTPRKrib; C: HECV wt plus stibogluconate; and D: cHECV/PTPRKrib plus stibogluconate. Cell were wounded at 6v for 30 seconds and traced immediately after wounding.*

Traces (in triplicate) of HaCaT (WT) response to stibogluconate over an arrange of concentrations.

Figure 6  3D modelling of HaCaT (WT) adhesion response to stibogluconate over an arrange of concentrations.

Figure 7 Traces (in duplicate) of HaCaT (WT) response to stibogluconate over an arrange of concentrations. Shown are traces at 100hz 1,000Hz, 12 hours, Ztheta96

Figure 8 *3D modelling of HaCaT (WT) migration response to stibogluconate over an arrange of concentrations. Shown at 1000Hz*

Using Rb modelling methods, a concentration dependent stimulation of cellular migration was also demonstrated. Shown are a 5-hour wounding assay, with mean plus SD displayed in the graph.

Figure 10  Shows the concentration related effect of Pentostam™ (GlaxoSmithKline), a commercially available form of stibogluconate on the migration of the cells.

1,2,3,4=HaCaT control; 5,6,7,8=HaCaT PTPRKrib
2,6=Penostram 1ug/ml; 3,7=Penstram 10ug/ml
HaCaT PTPRKrib Pentostam wounding-1

Figure 11  The effect of systemic administration of sodium stigbogluconate, via the I.P. route, on the rate of wound healing.

Effects of stibogluconate on wound healing in the db/sb model.
The compound was given topically every other day.

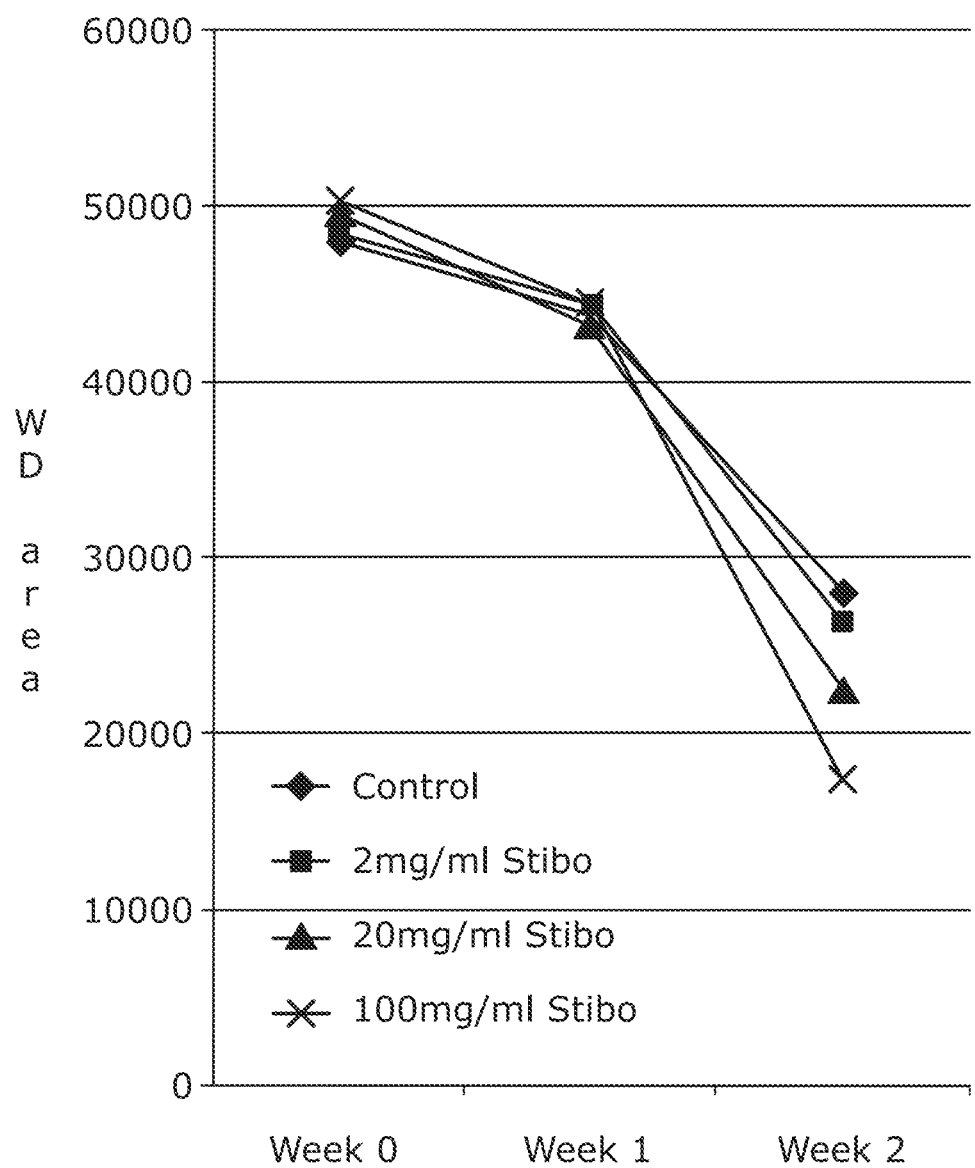
Figure 13  The effect of weekly delivery of Stibogluconate on the rate of wound healing.

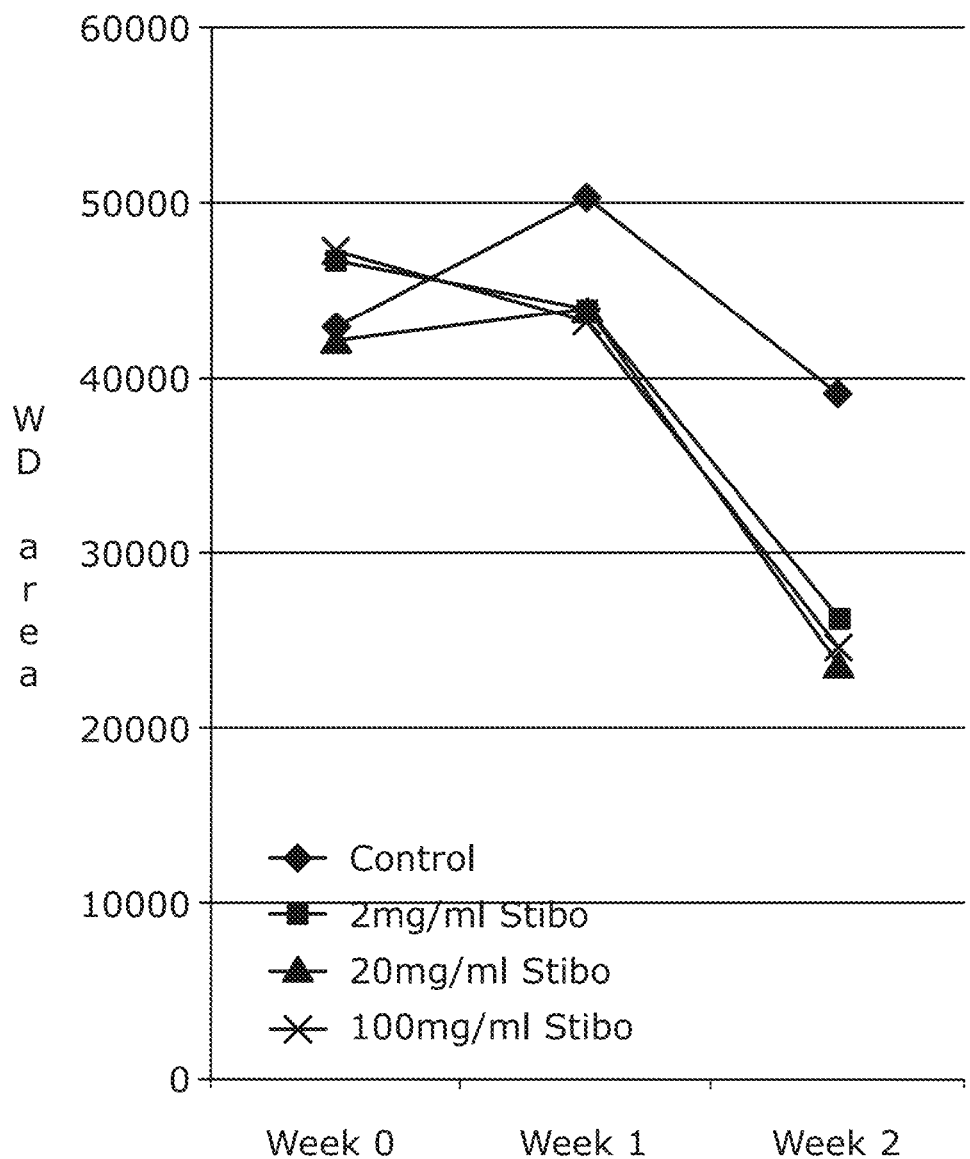
Figure 14  The effect of twice weekly delivery of Stibogluconate on the rate of wound healing.

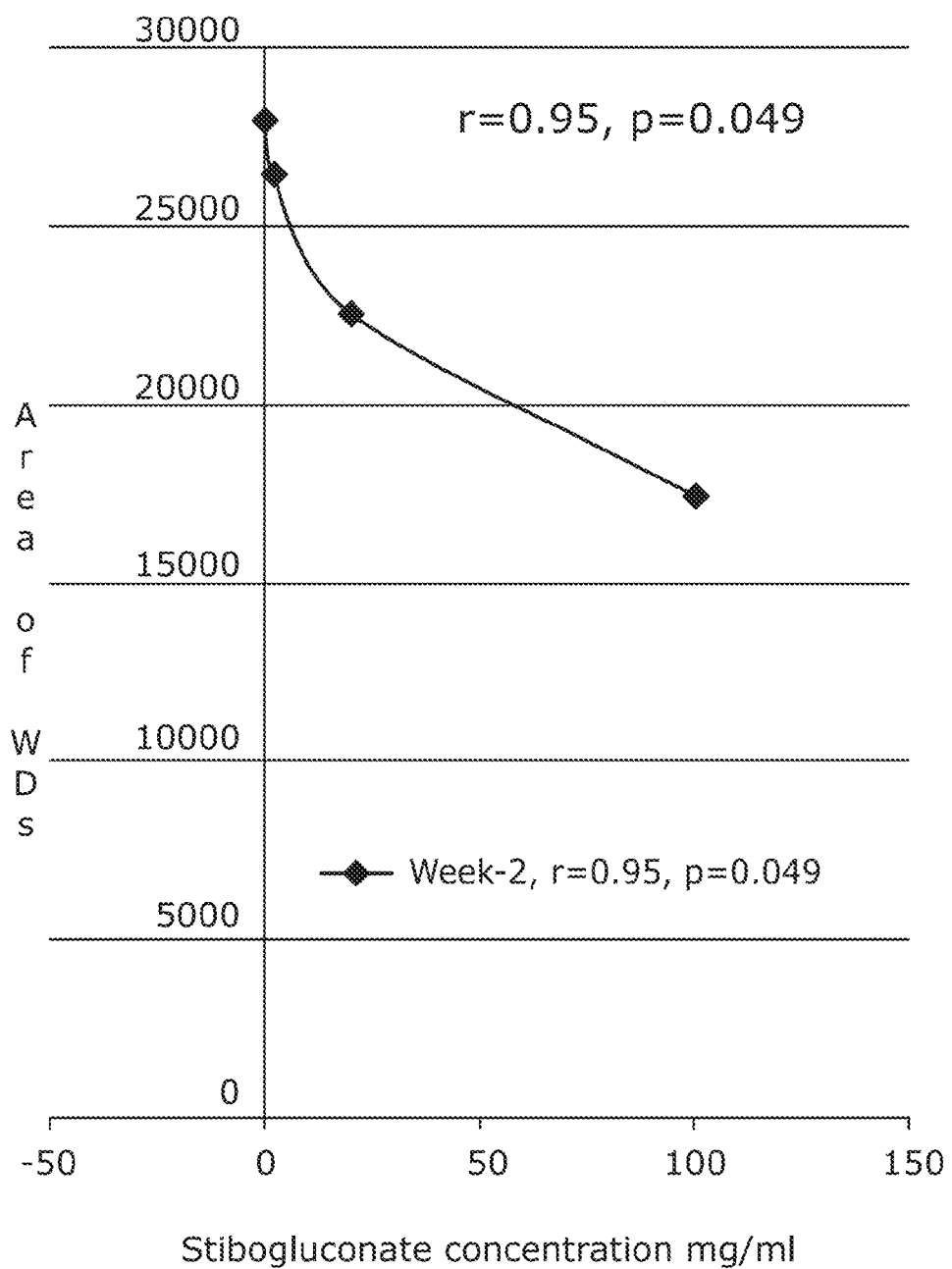
Figure 15  Scatter plot of stibogluconate concentration vs size of the wounds after two weeks of treatment (weekly).

cDNA sequence of human PTPRK 1 atggatacga ctgcggcggc ggcgctgcct gcttttgtgg cgctcttgct cctctctcct 61 tggcctctcc tgggatcggc ccaaggccag ttctccgcag gtggctgtac ttttgatgat 121 ggtccagggg cctgtgatta ccaccaggat ctgtatgatg actttgaatg ggtgcatgtt 181 agtgctcaag agcctcatta tctaccaccc gagatgcccc aaggttccta tatgatagtg 241 gactcttcag atcacgaccc tggagaaaaa gccagacttc agctgcctac aatgaaggag 301 aacgacactc actgcattga tttcagttac ctattatata gccagaaagg actgaatcct 361 ggcactttga acatattagt tagggtgaat aaaggacctc ttgccaatcc aatttggaat 421 gtgactggat tcacgggtag agattggctt cgggctgagc tagcagtgag ctccttttgg 481 cccaatgaat atcaggtaat atttgaagct gaagtctcag gagggagaag tggttatatt 541 gccattgatg acatccaagt actgagttat ccttgtgata aatctcctca tttcctccgt 601 ctaggggatg tagaggtgaa tgcagggcaa aacgctacat ttcagtgcat tgccacaggg 661 agagatgctg tgcataacaa gtatggctc cagagacgaa atggagaaga tataccagta 721 gcccagacta agaacatcaa tcatagaagg tttgccgctt ccttcagatt gcaagaagtg 781 acaaaaactg accaggattt gtatcgctgt gtaactcagt cagaacgagg ttccggtgtg 841 tccaattttg ctcaacttat tgtgagagaa ccgccaagac ccattgctcc tcctcagctt 901 cttggtgttg ggcctacata tttgctgatc caactaaatg ccaactcgat cattggcgat 961 ggtcctatca tcctgaaaga agtagagtac cgaatgacat caggatcctg gacagaaacc 1021 catgcagtca atgctccaac ttacaaatta tggcatttag atccagatac cgaatatgag 1081 atccgagttc tacttacaag acctggtgaa ggtggaacgg ggctcccagg acctccacta 1141 atcaccagaa caaatgtgc agaacctatg agaaccccaa agacattaaa gattgctgaa

Figure 16

1201 atacaggcaa gacggattgc tgtggactgg gaatccttgg gttacaacat tacgcgttgc 1261 cacacttta atgtcactat ctgctaccat tacttccgtg gtcacaacga gagcaaggca 1321 gactgtttgg acatggaccc caaagcccct cagcatgttg tgaaccatct gccaccttat 1381 acaaatgtca gcctcaagat gatcctaacc aatccagagg gaaggaagga gagtgaagag 1441 acaattattc aaactgatga agatgtgcct ggtcccgtac cagtaaaatc tcttcaagga 1501 acatcctttg aaaataagat cttcttgaac tggaaagaac ctttggatcc aaatggaatc 1561 atcactcaat atgagatcag ctatagcagt ataagatcat tgatcctgc agtcccagtg 1621 gctggacctc cccagactgt atcaaattta tggaacagta caccatgt ctttatgcat 1681 ctccaccctg gaaccacgta ccagtttttc ataagagcca gcacggtcaa aggctttggt 1741 ccagccacag ccatcaatgt caccaccaat atctcagctc caactttacc tgactatgaa 1801 ggagttgatg cctctctcaa tgaaactgcc accacaataa ctgtattgtt gagaccagca 1861 caagccaaag gtgctcctat cagtgcttat cagattgttg tggaagaact gcacccacac 1921 cgaaccaaga gagaagccgg agccatggaa tgctaccagg ttcctgtcac ataccaaaat 1981 gccatgagtg ggggtgcacc gtattacttt gctgcagaac tacccccggg aaacctacct 2041 gagcctgccc cgttcactgt gggtgacaat cggacctacc aaggcttttg gaaccctcct 2101 ttggctccgc gcaaaggata caacatctat ttccaggcga tgagcagtgt ggagaaggaa 2161 actaaaaccc agtgcgtacg cattgctaca aaagcagcaa cagaagaacc agaagtgatc 2221 ccagatcccg ccaagcagac agacagagtg gtgaaaatag caggaattag tgctggaatt 2281 ttggtgttca tcctccttct cctagttgtc atattaattg taaaaagag caaacttgct 2341 aaaaaacgca aagatgccat ggggaatacc cggcaggaga tgactcacat ggtgaatgca 2401 atggatcgaa gttatgctga tcagagcact ctgcatgcag aagatcctct ttccatcacc Figure 16 (continued)

2461 ttcatggacc aacataactt tagtccaaga tatgagaacc acagtgctac agcagagtcc 2521 agtcgccttc tagacgtacc tcgctacctc tgtgagggga cggaatcccc ttaccagaca 2581 ggacagctgc atccagccat cagggtagct gatttactgc agcacattaa tctcatgaag 2641 acatcagaca gctatgggtt caaagaggaa tatgagagct tttttgaagg acagtcagca 2701 tcttgggatg tagctaaaaa agatcaaaat agagcaaaaa accgatatgg aaacattata 2761 gcatatgatc actccagagt gattttgcaa cccgtagagg atgatccttc ctcagattat 2821 attaatgcca actatattga tggctaccag agaccaagtc attacattgc aacccaaggt 2881 cccgttcatg aaacagtgta tgatttctgg aggatgattt ggcaagaaca atctgcttgc 2941 attgtgatgg ttacaaattt agttgaggtt ggccgggtta aatgctataa atattggcct 3001 gatgatactg aagtttatgg tgacttcaaa gtaacgtgtg tagaaatgga accacttgct 3061 gaatatgtag ttaggacatt caccctggaa aggaggggggt acaatgaaat ccgtgaagtt 3121 aaacagttcc atttcacggg ctggcctgac catggagtgc cctaccatgc tacagggctg 3181 ctttccttta tccggcgagt caagttatca aaccctccca gtgctggccc catcgttgta 3241 cattgcagtg ctggtgctgg acgaactggc tgctacattg tgattgacat catgctagac 3301 atggctgaaa gagagggtgt tgttgatatt tacaattgtg tcaaagcctt aagatctcgg 3361 cgtattaata tggtccagac agaggaacag tacatttta ttcatgatgc catttagaa 3421 gcctgcttat gtggagaaac tgccatacct gtctgtgaat ttaaagctgc atatttgat 3481 atgattagaa tagactccca gactaactct tcacatctca aggatgaatt tcagactctg 3541 aattcagtca cccctcgact acaagctgaa gactgcagta tagcgtgcct gccaaggaac 3601 catgacaaga accgtttcat ggacatgctg ccacctgaca gatgtctgcc tttttaatt 3661 acaattgatg gggagagcag taactacatc aatgctgctc ttatggacag ctacaggcaa Figure 16 (continued)

3721 ccagctgctt tcatcgtcac acaatacccct ctgccaaaca ctgtaaaaga cttctggaga 3781 ttagtgtatg attatggctg tacctccatt gtgatgttaa acgaagtcga cttgtcccag 3841 ggctgccctc agtactggcc agaggaaggg atgctacgat atggccccat ccaagtggaa 3901 tgtatgtctt gttcaatgga ctgtgatgtg atcaaccgga ttttaggat atgcaatcta 3961 acaagaccac aggaaggtta tctgatggtg caacagtttc agtacctagg atgggcttct 4021 catcgagaag tgcctggatc caaaaggtca ttcttgaaac tgatacttca ggtggaaaag 4081 tggcaggagg aatgcgagga aggggaaggc cggacgatta tccactgcct aaatggtggc 4141 gggcgaagtg gcatgttctg tgctataggc atcgttgttg aaatggtgaa acggcaaaat 4201 gttgtcgatg ttttccatgc agtaaagaca ctgaggaaca gcaagccaaa catggtggaa 4261 gccccggagc aataccgttt ctgctatgat gtagctttgg agtacctgga atcatcttag Figure 16 (continued)

Protein sequence of human PTPRK

MDTTAAAALPAFVALLLLSPWPLLGSAQGQFSAGGCTFDDGPGACDYHQDLYDDFEWVHVSAQEP

HYLPPEMPQGSYMIVDSSDHDPGEKARLQLPTMKENDTHCIDFSYLLYSQKGLNPGTLNILVRVNKG

PLANPIWNVTGFTGRDWLRAELAVSSFWPNEYQVIFEAEVSGGRSGYIAIDDIQVLSYPCDKSPHFLR

LGDVEVNAGQNATFQCIATGRDAVHNKLWLQRRNGEDIPVAQTKNINHRRFAASFRLQEVTKTDQDL

YRCVTQSERGSGVSNFAQLIVREPPRPIAPPQLLGVGPTYLLIQLNANSIIGDGPIILKEVEYRMTSGS

WTETHAVNAPTYKLWHLDPDTEYEIRVLLTRPGEGGTGLPGPPLITRTKCAEPMRTPKTLKIAEIQAR

RIAVDWESLGYNITRCHTFNVTICYHYFRGHNESKADCLDMDPKAPQHVVNHLPPYTNVSLKMILTNP

EGRKESEETIIQTDEDVPGPVPVKSLQGTSFENKIFLNWKEPLDPNGIITQYEISYSSIRSFDPAVPVAG

PPQTVSNLWNSTHHVFMHLHPGTTYQFFIRASTVKGFGPATAINVTTNISAPTLPDYEGVDASLNETA

TTITVLLRPAQAKGAPISAYQIVVEELHPHRTKREAGAMECYQVPVTYQNAMSGGAPYYFAAELPPG

NLPEPAPFTVGDNRTYQGFWNPPLAPRKGYNIYFQAMSSVEKETKTQCVRIATKAATEEPEVIPDPA

KQTDRVVKIAGISAGILVFILLLLVVILIVKKSKLAKKRKDAMGNTRQEMTHMVNAMDRSYADQSTLHA

EDPLSITFMDQHNFSPRYENHSATAESSRLLDVPRYLCEGTESPYQTGQLHPAIRVADLLQHINLMKT

SDSYGFKEEYESFFEGQSASWDVAKKDQNRAKNRYGNIIAYDHSRVILQPVEDDPSSDYINANYIDG

YQRPSHYIATQGPVHETVYDFWRMIWQEQSACIVMVTNLVEVGRVKCYKYWPDDTEVYGDFKVTCV

EMEPLAEYVVRTFTLERRGYNEIREVKQFHFTGWPDHGVPYHATGLLSFIRRVKLSNPPSAGPIVVHC

SAGAGRTGCYIVIDIMLDMAEREGVVDIYNCVKALRSRRINMVQTEEQYIFIHDAILEACLCGETAIPVC

EFKAAYFDMIRIDSQTNSSHLKDEFQTLNSVTPRLQAEDCSIACLPRNHDKNRFMDMLPPDRCLPFLI

TIDGESSNYINAALMDSYRQPAAFIVTQYPLPNTVKDFWRLVYDYGCTSIVMLNEVDLSQGCPQYWP

EEGMLRYGPIQVECMSCSMDCDVINRIFRICNLTRPQEGYLMVQQFQYLGWASHREVPGSKRSFLK

LILQVEKWQEECEEGEGRTIIHCLNGGGRSGMFCAIGIVVEMVKRQNVVDVFHAVKTLRNSKPNMVE

APEQYRFCYDVALEYLESS

Figure 16 (continued)

MOLECULAR TARGETS FOR HEALING OR TREATING WOUNDS

This application is a divisional patent application claiming priority to U.S. patent application Ser. No. 14/000,532 filed on Sep. 16, 2013, which is the national stage of international patent application no. PCT/GB2012/050362 filed on Feb. 17, 2012, which in turn claims priority from British Patent Application Ser. No. 1103898.1 filed on Mar. 8, 2011, the disclosures of which are incorporated herein by reference in their entirety.

TECHNICAL FIELD

The present invention relates to at least one molecular target for healing or treating wounds and, in particular, human wounds. More particularly still, the molecular target has application in the treatment of chronic wounds. Further, the invention concerns a novel therapeutic for treating said wounds and a novel gene therapy approach, involving said molecular target, for treating said wounds. Additionally, the invention concerns a method for treating wounds using said therapeutic or said gene therapy.

BACKGROUND

In one form or another, chronic and poorly healing wounds constitute a major burden on the UK health system. Moreover, in certain member countries of the EU health expenses relating to wound healing are already approaching the third most expensive drain on health care funding.

A Chronic wound is herein defined as one exhibiting delayed or defective healing which does not progress through the predictable stages of the healing process (as described below). Commonly, chronic wounds are classified into three broad categories: venous ulcers, diabetic, and pressure ulcers. Long-term venous insufficiency accounts for 70% to 90% of chronic wounds and commonly affects the elderly. Venous insufficiency results in venous hypertension, in which blood flow is abrogated resulting in subsequent ischaemia. Venous insufficiency can occur as a result of obstructions to venous outflow or reflux due to valve damage. Following a period of ischaemia, tissue reperfusion can result in reperfusion injury, causing the tissue damage that leads to wound formation.

Chronic foot ulcers are a major complication of diabetes, accounting for up to 25% of all hospital admissions involving diabetes, and at a cost to the UK National Health Service of £250M annually. Chronic foot ulcers cause substantial morbidity, impair the quality of life, and are the major cause of lower limb amputation. Despite careful attention to foot care, as many as 25% of diabetics develop foot ulcers in their lifetimes. The causes of lower limb ulceration are the same in diabetics as in non-diabetics, namely neuropathy, ischaemia and trauma. However, this "pathogenic triad" predisposes wounds to infection, which can also contribute to the non-healing nature of the wounds.

Pressure wounds are another major resource health cost. They are typically caused by failure to provide routine nursing or medical care. In the UK 412,000 people are affected annually by this sort of wound at a cost of £1.4-2.1 billion.

Furthermore, chronic wounds can also be categorised by whether they are caused by surgery, burns, dermatitis, vasculitis or radiation.

Current wound treatment strategies involve removing pressure from the area, debridement, wound dressing and management of infection: surgical resection and vascular reconstruction may be required in more advanced disease, which ultimately may necessitate amputation. These strategies commonly seek to address problems that are associated with chronic wounds, such as bacterial load, ischaemia, and imbalance of proteases, all of which can further affect the wound healing process.

The healing of a wound is controlled by complex biological processes that involve a diverse number of cell types; complex interactions between cells and tissues; the activation of the immune system and the activation of the angiogenic process. Moreover, all of these processes involve a large number of molecules.

A typical healing process can be divided into 5 distinct, but closely related, stages: clotting stage, acute inflammation stage, matrix deposition stage, capillary formation stage and re-epithelialisation stage. A diverse number of factors are involved in and control each of these stages. Deficiencies in any aspect of the process may result in defective wound healing. Thus, a 'normal' healing process may be defective as a result of either intrinsic or external factors, which manifest as 'abnormal non-healing' or 'chronic' wounds. It is these chronic or 'non-healing' wounds that present the greatest challenge to the quality of a patient's life and mounting expenses to the healthcare system.

A chronic wound often arises from failure to progress through the normal stages of wound healing, whereby an initial injury resulting in a wound cannot subsequently be repaired. Changes occur within the molecular environment of a chronic wound, such as high levels of inflammatory cytokines or proteases, and low levels of growth factors, these changes detain or terminate the healing process and increase the potential for septic infections. By enhancing or manipulating factors that contribute to wound healing it may therefore be possible to correct the process, thereby reducing the likely occurrence of a chronic wound, or accelerate its subsequent repair.

PTPRK

Protein tyrosine phosphatise receptor type K, PTPRK, is also known as DKFZp686C2268, DKFZp779N1045 and R-PTP-kappa. It is a member of the protein tyrosine phosphatase (PTP) family. PTPs are known to be signalling molecules that regulate a variety of cellular processes including cell growth, differentiation, mitotic cycle, and oncogenic transformation. PTPRK possesses an extracellular region, a single transmembrane region, and two tandem catalytic domains, and thus represents a receptor-type PTP. The extracellular region contains a meprin-A5 antigen-PTP mu (MAM) domain, an Ig-like domain and four fibronectin type III-like repeats. Moreover, PTPRK has been shown to mediate homophilic intercellular interaction, possibly through the interaction with beta- and gamma-catenin at adherens junctions. Expression of the PTPRK gene has been found to be stimulated by TGF-beta 1, which may be important for the inhibition of keratinocyte proliferation. In cancer, PTPRK has been found to be suppressed in aggressive tumours as shown by our recent study in breast cancer (Sun et al, SABCS, Cancer Res 2010).

While the biochemical functions of the PTP family is known to some degree, the therapeutic implication of the PTPRK enzyme has rarely been explored, particularly in relation to wound healing.

We, therefore, have surprisingly discovered that PTPRK has a role to play in wound healing. Indeed, we have discovered that the expression of this protein impedes the wound healing process. Moreover, the inhibition of PTPRK promotes wound healing.

Inhibitors of PTPRK are known. The most readily available is a salt of stibogluconate. Sodium stibogluconate is a medicine used to treat leishmaniasis, a disease resulting from infection by one of over 20 different species of the *Leishmania* species of parasite. Sodium Stibogluconate belongs to the class of medicines known as the pentavalent antimonials. Whilst its exact paracidal effect on the *Leishmania* parasite is unknown it is thought that the parasite is killed by inhibition of glucose catabolism resulting in reduced ATP synthesis, thereby decreasing subsequent macromoleular synthesis and preventing replication.

Sodium stibogluconate is sold in the United Kingdom as PENTOSTAM™ (manufactured by GlaxoSmithKline) and is currently only available for administration by injection. Unfortunately, widespread resistance to this medicine has limited the utility of sodium stibogluconate, and in many parts of the world, amphotericin or miltefosine is used instead to treat leishmaniasis.

In summary, we have identified at least one molecular target for treating wounds and in particular human wounds. More particularly, but not exclusively, said molecular target has application in the treatment of chronic wounds. The molecular target is PTPRK and therefore the invention relates to a novel therapeutic comprising an inhibitor of either, or both, PTPRK expression or PTPRK activity. In the former instance, the invention involves a novel gene therapy approach and in the latter instance a novel protein therapy approach. Accordingly, the invention also relates to a novel therapeutic comprising an inhibitor of either, or both, PTPRK expression or PTPRK activity. In the former instance, the invention involves a novel gene therapy approach and in the latter instance a novel protein therapy approach.

Reference herein to PTPRK, is reference to a gene or protein whose identity is shown in FIG. 16.

Our invention can improve the quality of a patient's life by ensuring that new wounds do not deteriorate into a chronic state and existing chronic wounds can be treated in a way that actively promotes healing.

SUMMARY

Accordingly, in one aspect of the invention there is provided a therapeutic comprising an inhibitor of either, or both, PTPRK gene expression or PTPRK protein activity for use in the treatment of wounds.

In the former instance, the invention involves a novel gene therapy approach and in the latter instance a novel protein therapy approach. Thus, in one embodiment the novel therapeutic comprises an inhibitor of PTPRK gene expression, this inhibitor can be either anti-sense DNA or RNA, siRNA, or ribozymes, either naked or in the form of plasmid and viral vectors. Those skilled in the art are aware of the aforementioned inhibitory molecules and so would be able to work the invention once they knew that expression of PTPRK contributed to the chronic wound phenotype. However, in another embodiment the novel therapeutic comprises an inhibitor of PTPRK protein function, this inhibitor can be either a PTPRK binding agent that binds, either reversibly or irreversibly, to inhibit protein function such as an antibody or a known, or synthesized, PTPRK antagonist; or an agent that works upstream or downstream of the PTPRK signalling mechanism to inhibit PTPRK signalling and so negate the effects of expression of PTPRK protein in wound tissue. Those skilled in the art are aware of the aforementioned inhibitory molecules and so would be able to work the invention once they knew that expression of PTPRK contributed to the chronic wound phenotype.

In a preferred embodiment of the invention the therapeutic comprises a PTPRK gene inhibitor such as transgene 1 or transgene 2 or transgene 3 described herein. These molecules are termed anti-PTPRK ribozyme/RNA transgenes.

```
Transgene 1 is produced by transcription of the

PTPRK gene using the following short oligos:

Anti-PTPRK transgene1F
                                        (SEQ ID NO: 1)
Ctgcagagtgagttacacagcctgatgagtccgtgagga And Anti-PTPRK transgene1R
                                        (SEQ ID NO: 2)
ActagtgacaaaaactgaccaggatttgtAtttcgtcctcacggact.

Transgene 2 is produced by transcription of the

PTPRK gene using the following short oligos:

Anti-PTPRK transgene2F
                                        (SEQ ID NO: 3)
Ctgcaggatgataggaccatcgccaatctgatgagtccgtgagga and Anti-PTPRK transgene2R
                                        (SEQ ID NO: 4)
ActagtgatccaactaaatgccaactcgAtttcgtcctcacggact.

Transgene 3 is produced by transcription of the

PTPRK gene using the following short oligos:

Anti-PTPRK transgene3F
                                        (SEQ ID NO: 5)
Ctgcagtttgctctttttttacaattaatatctgatgagtccgtgagga and Anti-PTPRK transgene3R
                                        (DEQ ID NO: 6)
ActagttcatcctccttctcctagttGtttcgtcctcacggact.
```

These products are antisense-hammerhead ribozyme also known as antisense-hammerhead RNA, ideally they are flanked by selected restriction sites such as pstI and SpeI and more ideally still they are cloned into a cloning vector such as pEF6/V5His-TOPO vector (Invitrogen),

```
The sequence structure of transgene 1 is:
                                        (SEQ ID NO: 7)
5'Ctgcagagtgagttacacagcctgatgagtccgtgaggacgaaa tacaaatcctggtcagtttttgtt actagt'3

The sequence structure of transgene 2 is:
                                        (SEQ ID NO: 8)
5'Ctgcaggatgataggaccatcgccaatctgatgagtccgtgaggac gaaatcgagttggcatttagttggatcactagt'3

The sequence structure of transgene 3 is:
                                        (SEQ ID NO: 9)
Ctgcagtttgctctttttttacaattaatatctgatgagtccgtgaggac gaaacaactaggagaaggaggatgaactagt'3
```

In a preferred embodiment of the invention the therapeutic comprises a commercially available PTPRK protein inhibitor such as, without limitation, Stibogluconate (GSK) or (Santa Cruz Biotechnologies Inc., Tocris and Sigma-Aldrich).

In a further preferred embodiment of the invention the therapeutic comprises a commercially available PTPRK protein inhibitor, such as PENTOSTAM™ (GlaxoSmithKline).

The therapeutic of the invention is for use in treating, ideally, mammalian wounds, more ideally chronic mammalian wounds, and, more ideally still, chronic human wounds. Chronic wounds that are preferably treated using the invention are venous ulcers, diabetic ulcers, and pressure ulcers. Preferably, the wounds to be treated are non-parasitic i.e. not caused by or occupied by parasites.

An antibody for use in the invention is most ideally a monoclonal antibody or a humanised antibody.

In the above aspects and embodiments of the invention the therapeutic is formulated for topical application.

Alternatively, in the above aspects and embodiments of the invention the therapeutic is formulated for oral application.

Alternatively again, in the above aspects and embodiments of the invention the therapeutic is formulated for application to a dressing or impregnation in a dressing.

The therapeutic of the invention may be administered in combination with an antibiotic or antibacterial agent. Numerous such agents are known and suitable choices will be familiar to skilled practitioners.

In yet another aspect of the invention, there is provided a pharmaceutical composition for use in treating wounds comprising a therapeutic of the invention together with a pharmaceutically acceptable carrier.

Other active materials may also be present in the pharmaceutical composition, as may be considered appropriate or advisable for the wound being treated. For example, the composition may also contain an emollient, or the like.

The carrier, or, if more than one be present, each of the carriers, must be acceptable in the sense of being compatible with the other ingredients of the formulation and not deleterious to the recipient.

The formulations include those suitable for topical (including eye drops), oral (including buccal and sublingual), rectal, nasal or vaginal administration and may be prepared by any methods well known in the art of pharmacy.

The composition may be prepared by bringing into association the therapeutic of the invention and the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a therapeutic of the invention in conjunction or association with a pharmaceutically or veterinarily acceptable carrier or vehicle.

For topical application to the skin, compounds of conventional use may be made up into a cream, ointment, jelly, solution or suspension etc. Cream or ointment formulations that may be used for the composition are conventional formulations well known in the art, for example, as described in standard text books of pharmaceutics such as the British Pharmacopoeia.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

Other formulations suitable for oral administration include lozenges comprising the active agent in a flavoured or inert base and mouthwashes comprising the active agent in a suitable liquid carrier.

In a further aspect of the invention there is provided a method for treating a mammalian wound, typically a chronic wound, which method comprises: administering to said wound a therapeutic that inhibits either, or both of, PTPRK gene expression or PTPRK protein activity.

Additionally, or alternatively, the further aspect of the invention also, or alternatively, comprises a novel method for treating a mammalian wound, typically a chronic wound, which method comprises:

administering to said wound a therapeutic that inhibits either, or both of, PTPRK gene expression or PTPRK protein activity.

According to yet a further aspect of the invention there is provided a kit for treating a wound, preferably a chronic wound, wherein said kit comprises:

(a) at least one therapeutic as above described; and
(b) at least one dressing for applying to said wound.

According to a yet further aspect of the invention there is provided a combination therapeutic for treating a wound comprising an inhibitor of PTPRK gene expression and an inhibitor of PTPRK protein activity.

According to a further aspect of the invention there is provided a therapeutic for treating a wound comprising an inhibitor of PTPRK protein, or a homologoue thereof.

According to a further aspect of the invention there is provided use of an inhibitor of PTPRK protein, or a homologoue thereof, in the manufacture of a medicament for treating a wound.

According to a further aspect of the invention there is provided use of an inhibitor of PTPRK, or a homologue thereof, for treating a wound.

The term "homologue" as used herein refers to amino acid sequences which have a sequence at least 50% homologous to the amino acid sequence of PTPRK and which retain the biological activity of the PTPRK sequence. It is preferred that homologues are at least 75% homologous to the PTPRK peptide sequence and, in increasing order of preference, at least 80%, 85%, 90%, 95% or 99% homologous to the PTPRK peptide sequence.

Treatment of a wound described herein includes reference to human or veterinary use.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The present invention will now be described by way of the following examples with particular reference to FIGS. 1-21 wherein:

FIG. 1. Shows the secondary structure of human PTPRK mRNA;

FIG. 2A. Shows HaCaT cells after lost PTPRK by way of anti-PTPRK transgenes showed an increase in cell adhesion. Shown are traces at 4000 Hz and 3D modelling at 4,000 Hz and 500 Hz;

FIG. 2B. Shows HaCaT cells after lost PTPRK by way of anti-PTPRK transgenes showed an increase in cell adhesion. Shown are traces at 32,000 Hz and 3D modelling at 4,000 Hz and 500 Hz;

FIG. 13. Shows the effect of weekly delivery of Stibogluconate on the rate of wound healing;

FIG. 14. Shows the effect of twice weekly delivery of Stibogluconate on the rate of wound healing;

FIG. 15. Shows a scatter plot of stibogluconate concentration vs size of the wounds after two weeks of treatment (weekly);

FIG. 16. shows the amino acid and cDNA sequence structure of PTPRK;

DETAILED DESCRIPTION

Materials and Procedure

Cells

Figure 3:
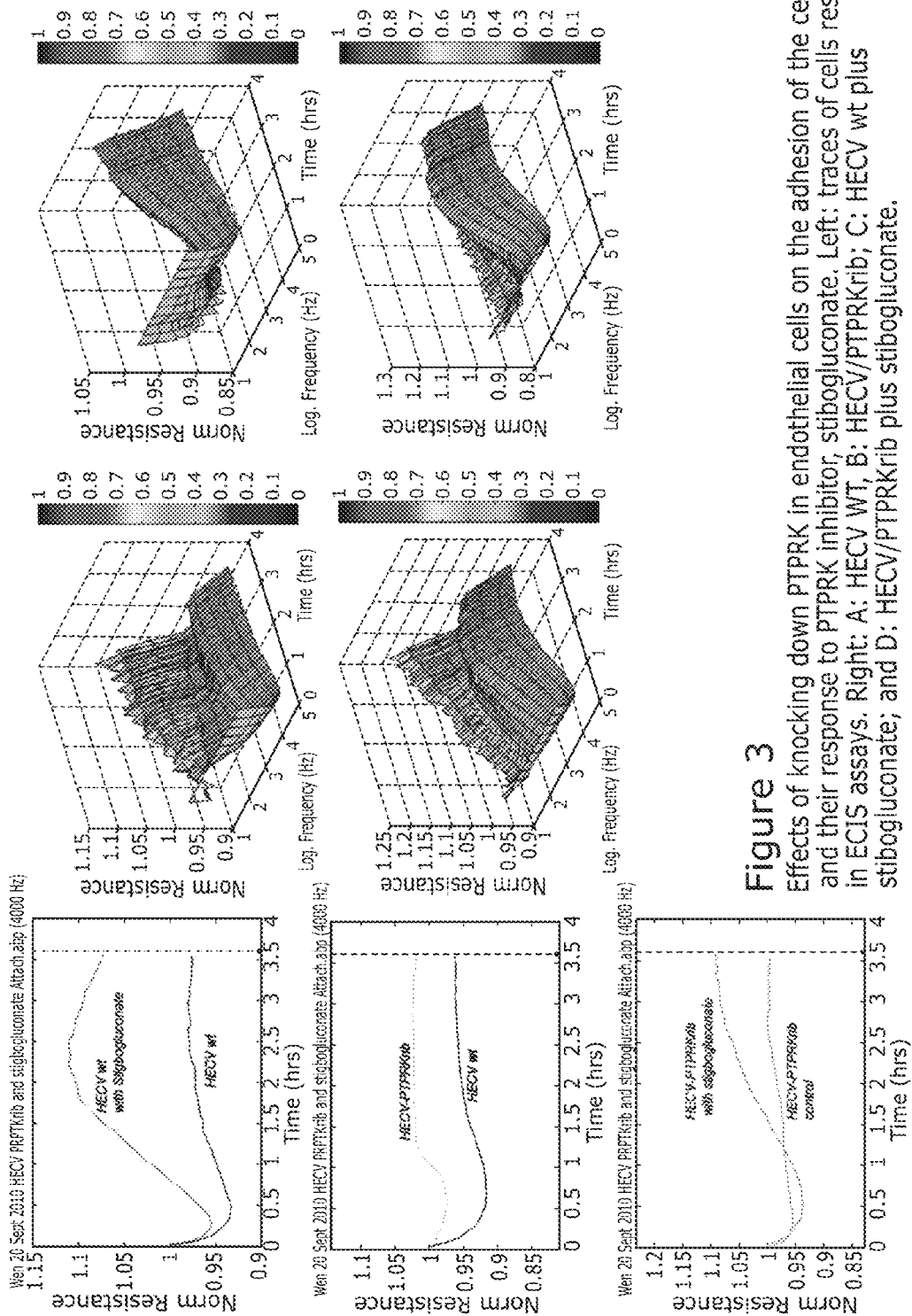
FIG. 3. Shows effects of knocking down PTPRK in endothelial cells on the adhesion of the cells and their response to PTPRK inhibitor, stibogluconate. Left: traces of cells response in ECIS assays. Right: A: HECV WT, B: HECV/PTPRKrib; C: HECV wt plus stibogluconate; and D: HECV/PTPRKrib plus stibogluconate.

HaCaT, a human keratinocyte cell line was purchased from the German Cancer Centre, HECV, a human vascular endothelial cells from Interlab, Milan, Italy, DB/DB mice from Harlan UK.

Construction of Ant-Human PTPRK Ribozyme Transgenes

The transgenes were based on the human PTPRK mRNA secondary structure (FIG. 1). Three transgenes were generated, targeting ATC and GTC sites, using respective oligos listed in Table 1. Ribozymes were generated by way of touchdown PCR, followed by verification using 2% agarose gels. The correct ribozymes were ligated into a pEF6/V5His-TOPO vector (Invitrogen), followed by transformation of the ligated product to Top10 *E. Coli*. After heat shock for 30 seconds and recover over ice for 2 minutes, the bacteria was resuspended in SOC medium and allow to grow on a shaker (200 rpm) for 1 hour. The transformed bacteria were then plated over LB agar dishes which contained 100 ug/ml Ampicillin. After incubating the plate at 37° C. overnight, discreet colonies were identified and screened for the presence of the ribozyme and the orientation of the insert, by using orientation specific PCR, using T7F primers vs RBBMR and RBTPF primers. Correct colonies were picked, grew up in LB medium in the presence of Ampicillin. Plasmids were extracted, purified and further verified by direction specific PCR (using RBTOP vs T7F and RBBMR).

Generation of Sublines of Human Keratinocytes and Endothelial Cells with Differential Expression of PTPRK HaCaT and HECV cells, which were positive for PTPRK, were transfected with anti-PTPRK transgenes by way of electroporation (270 v). After selection with a selection medium (DMEM with 10 ug/ml blasticidin) for 10 days, clones of selected cells were pooled and used for subsequent analysis.

In Vivo Tolerance Test

The first tolerance test was conducted on the CD-1 athymic (Charles River Laboratories). Briefly, CD-1 of 4-6 weeks old, 20 g in weight, were housed in filter topped cages. Sodium stibogluconate a known PTPRK inhibitor was injected, via the intraperitoneal route, on a daily basis. The compound was given at 100 final concentration (equivalent to ~10 mg/kg body weight) in 100 ul in volume. CD-1 were observed daily, weighed twice weekly. An additional tolerance and efficacy test was carried out using the db/db strain.

In Vivo Efficacy Test and Wound Healing

The diabetic strain of db/db was obtained from Harlan. 4-6 weeks old with body weight at 20 g were used. Creation of a wound was according to a recently described method. Briefly, after being housed for a week, the db/db were first ear-pieced using an puncher, in order to create a wound (hole) of 1 mm in diameter. The following day after wound creation, all the db/db were weighed and the wound was photographed using a digital camera. Treatment was given systemically (by IP injection) or topically (by manually applying the compound in gel into the wound area). Both treatments were given every other day, twice weekly or weekly. Images were obtained weekly. The size of the wounds was determined using an image analysis software and is shown here as the area in pixels.

Effects of Knocking Down PTPRK on the Function of Cells

Three models of ECIS instrument were used: ECIS 9600 for screening and ECIS1600R and ECIS Z8 for modelling. In all systems, 8W10 arrays were used (Applied Biophysics Inc., Troy, N.Y., USA) (Giaever and Keese 1991, Kees et al 2004). Following treating the array surface with a Cysteine solution (or array stabilization procedure for ECIS Z8), the arrays were incubated with complete medium for 1 hr Electric changes were continuously monitored for up to 24 hrs. In the 9600 system, the monitoring was at fixed 30 Hz. In the 1600R and ECIS Zθ systems, cells were monitored at 62.5, 125, 250, 500, 1,000, 2,000, 4,000, 8,000, 16,000, 32,000 and 64,000 Hz. The adhesion was analysed by the integrated Rb modelling method.

Results

Knocking Down PTPRK from HaCaT and Endothelial Cells Resulted in an Acceleration of Cell Adhesion and Migration It was found that after knocking down PTPRK in HaCaT cells, there was a rapid increase in cell adhesion, FIGS. 2A-2B. Endothelial cells, after loss of PTPRK, showed a high rate of adhesion using an ECIS assay. Likewise, HECV/WT when treated with stibogluconate, also showed a rapid adhesion to the surface of the electrode. It is interesting to observe that HECV/PTPRKrib cells' response to stibogluconate was markedly reduced compared with that of HECV/WT. The similar changes in cellular migration were seen using the electric wounding assay of the endothelial cell model, FIG. 3 and FIG. 4.

Figure 5:
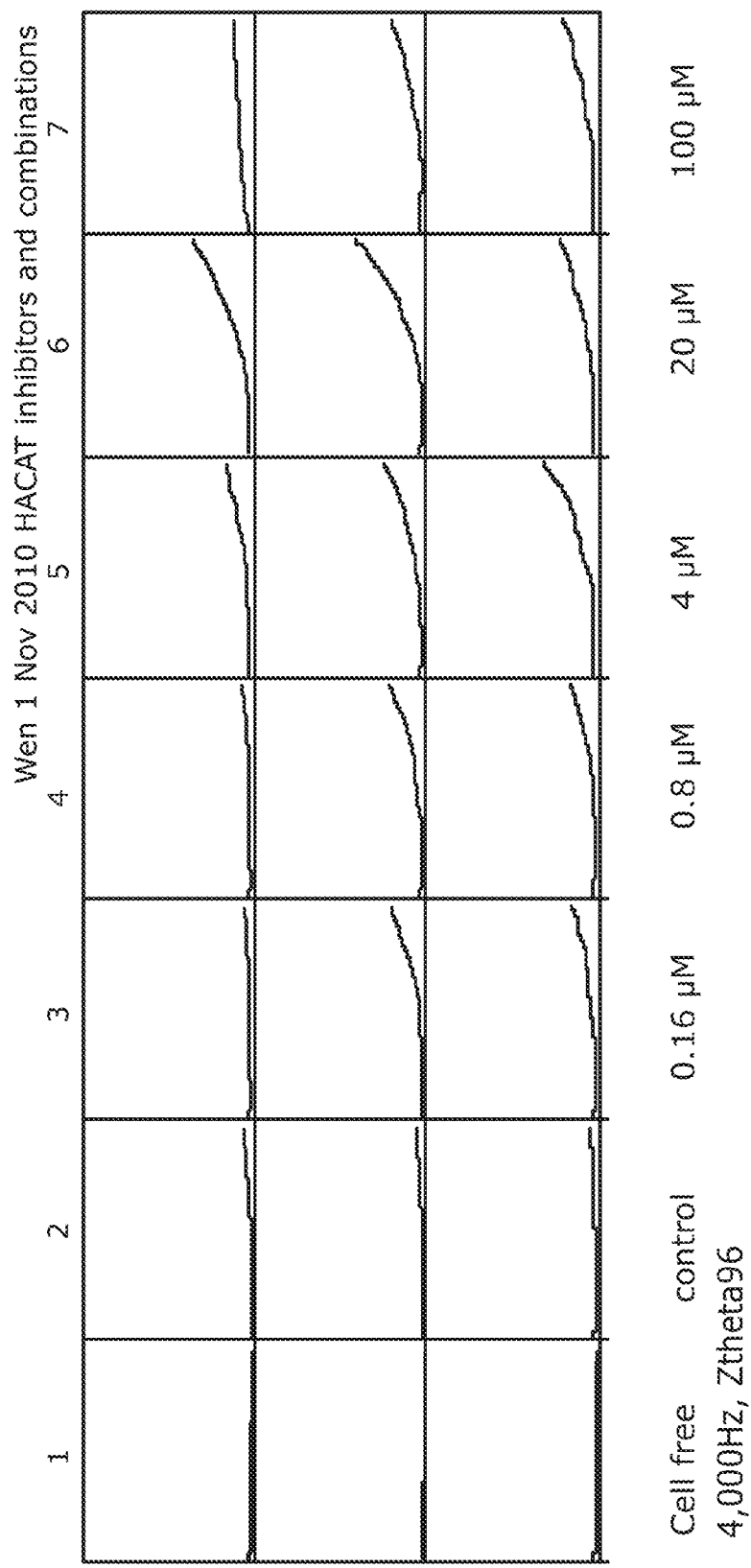
FIG. 5. Shows Traces (in triplicate) of HaCaT (WT) response to stibogluconate over an arrange of concentrations.
Figure 6:
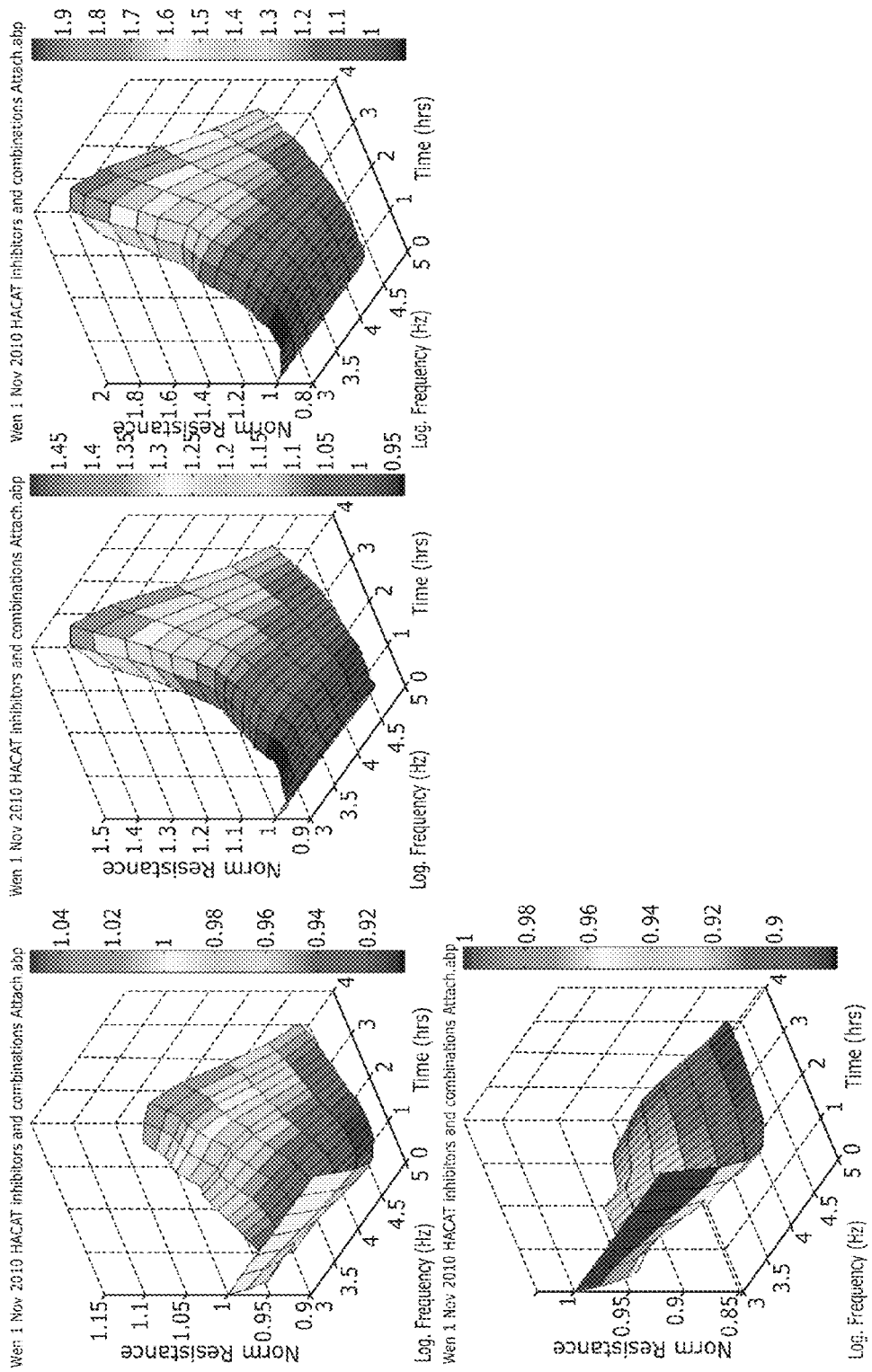
FIG. 6. Shows 3D modelling of HaCaT (WT) adhesion response to stibogluconate over an arrange of concentrations.
Figure 7:
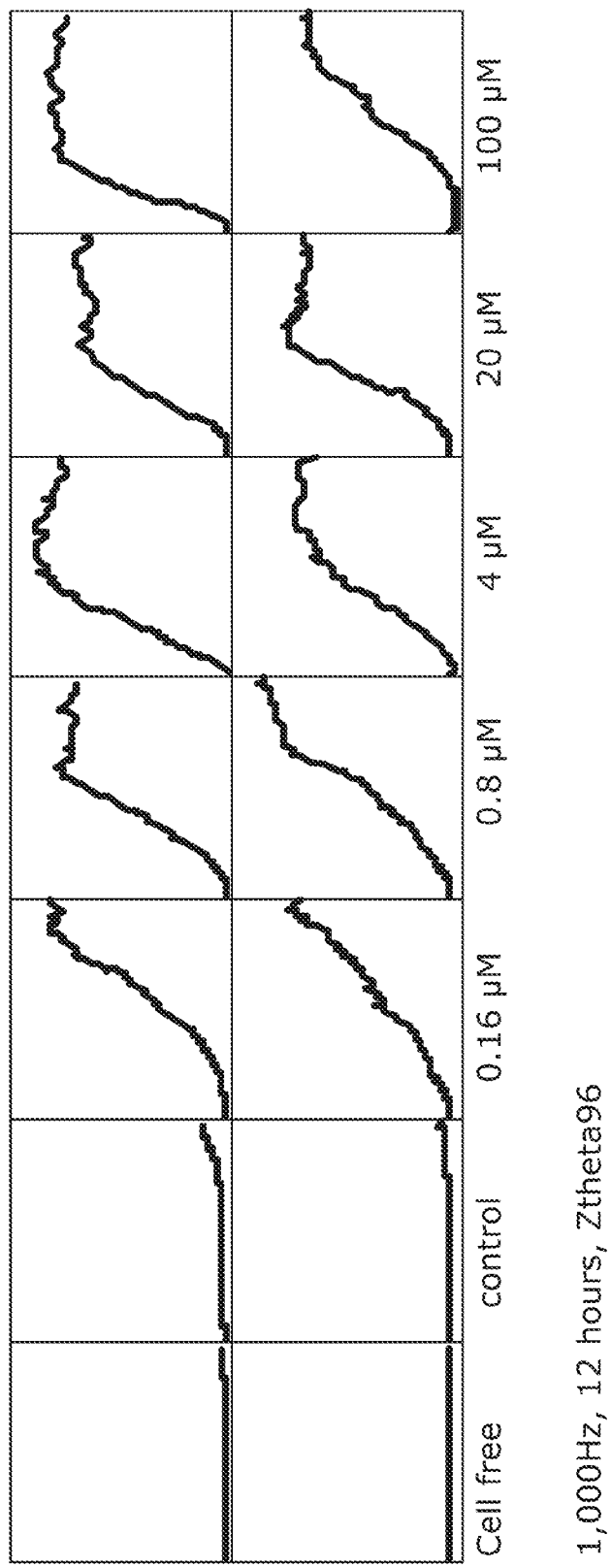
FIG. 7. Shows traces (in duplicate) of HaCaT (WT) response to stibogluconate over an arrange of concentrations. Shown are traces at 100 hZ.
Figure 8:
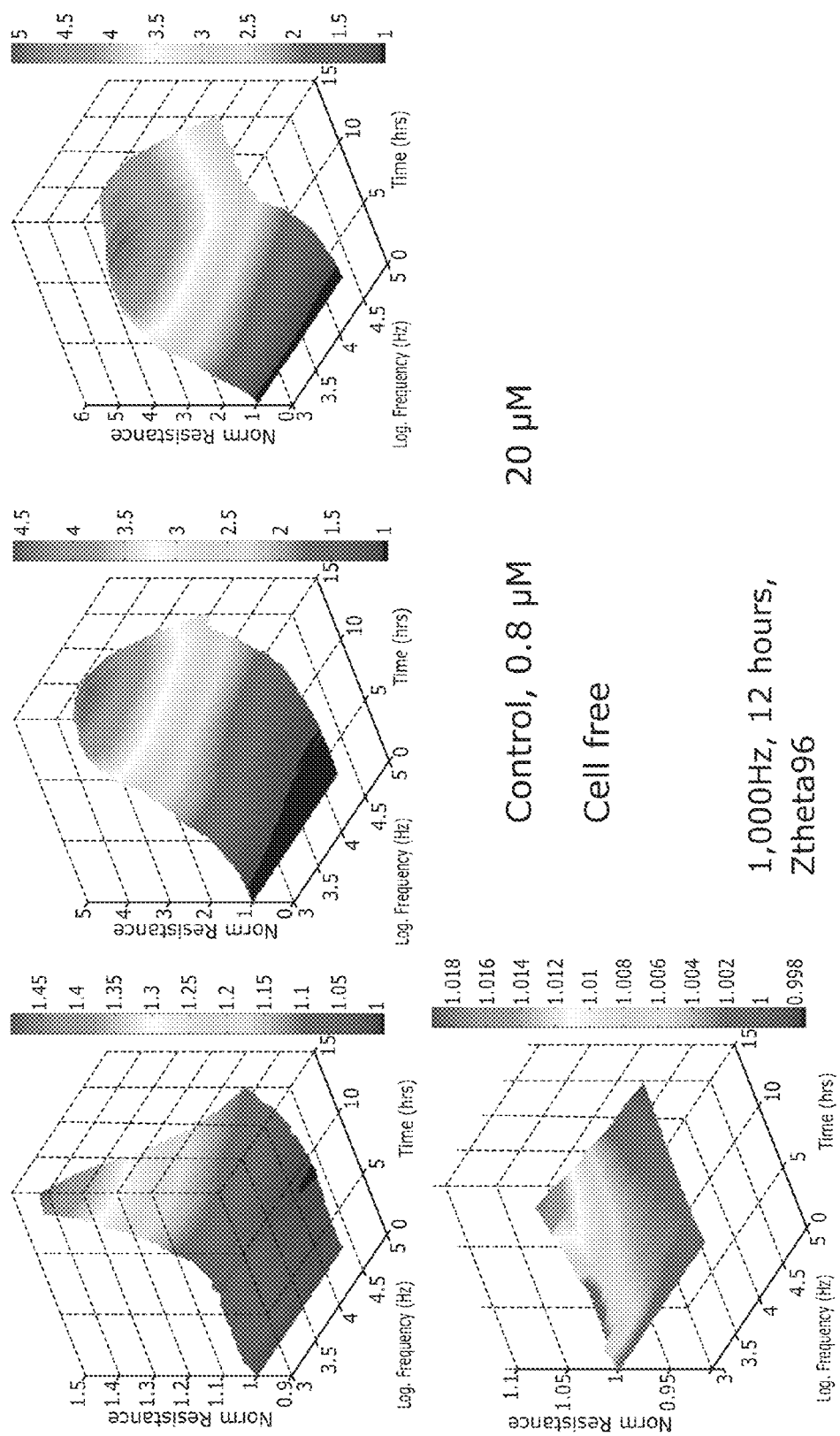
FIG. 8. Shows 3D modelling of HaCaT (WT) migration response to stibogluconate over an arrange of concentrations. Shown at at 1000 Hz.
Figure 9:
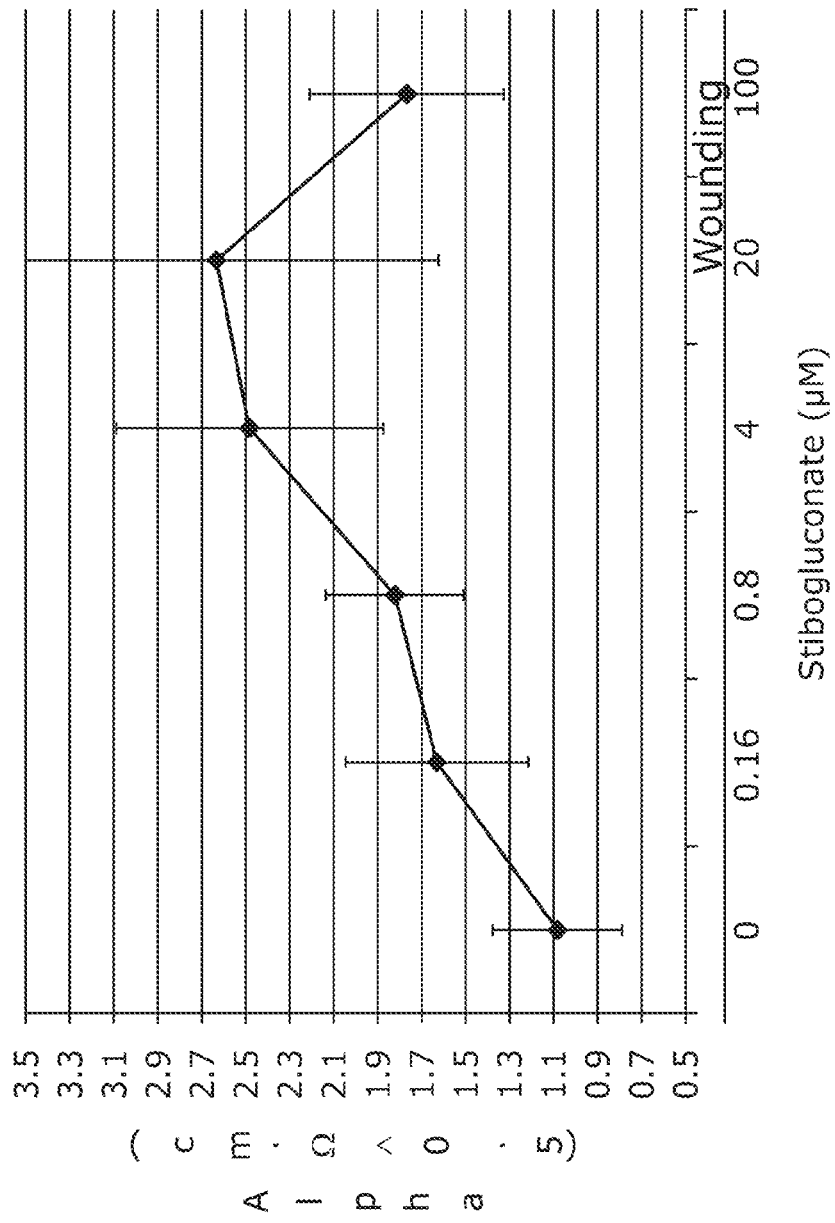
FIG. 9. Shows Using Rb modelling methods, a concentration dependent stimulation of cellular migration was also demonstrated. Shown are a 5-hour wounding assay, with mean plus SD displayed in the graph.

Human Keratinocytes Showed a Dose Dependent Response to PTPRK Inhibitor Stibogluconate Using the ECIS Theta96 model, we tested the response of cells to stibugluconate over a range of concentrations. HaCaT cells responded over the range of concentrations tested in that there was an increase in cell adhesion between 0.16-20 uM with 20 uM showing the maximum effects, FIGS. 5 & 6. Likewise, the cells also responded to stibogluconate by increasing their migration from concentrations as low as 160 nM to 100 uM, FIGS. 7, 8 & 9.

Figure 10:
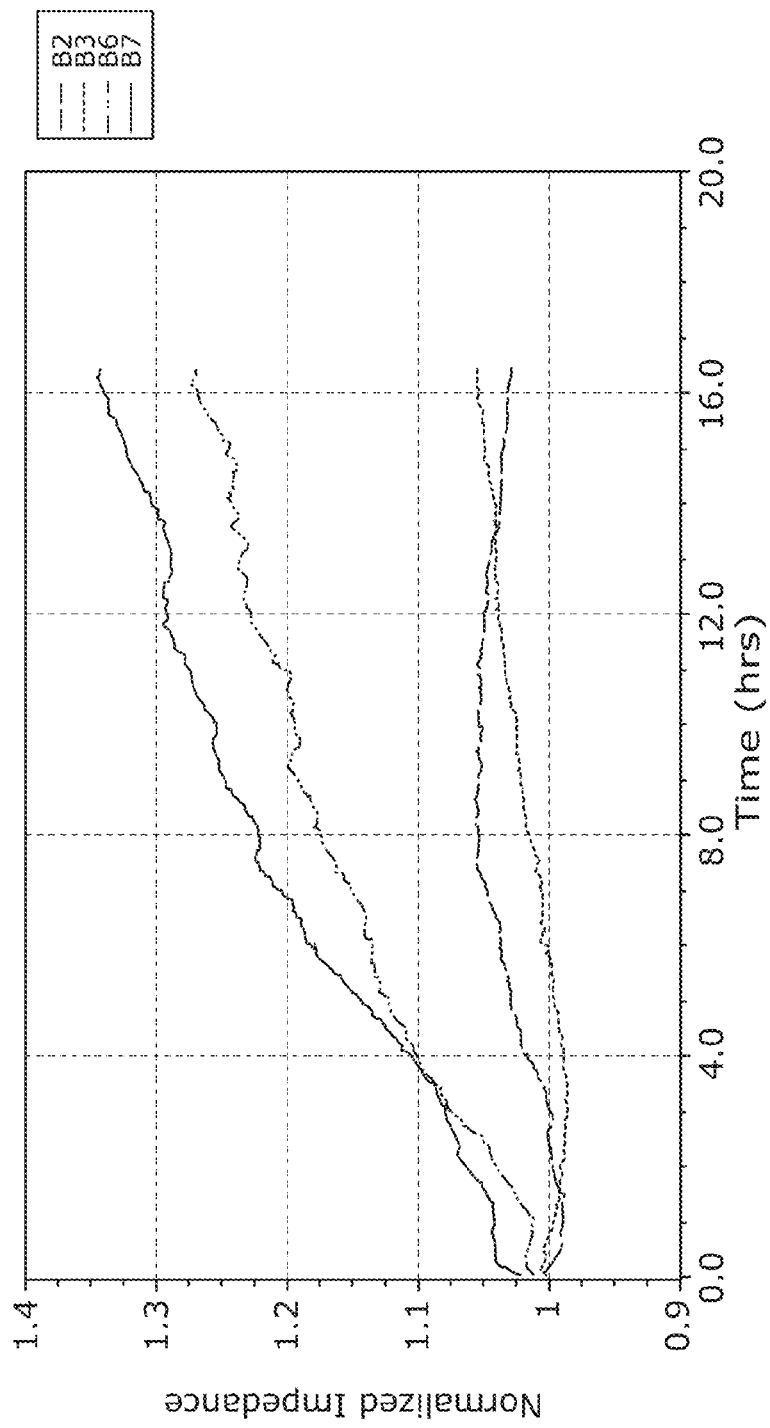
FIG. 10. Shows the concentration related effect of PENTOSTAM™ (GlaxoSmithKline), a commercially available form of stibogluconate on the migration of the cells.
Figure 11:
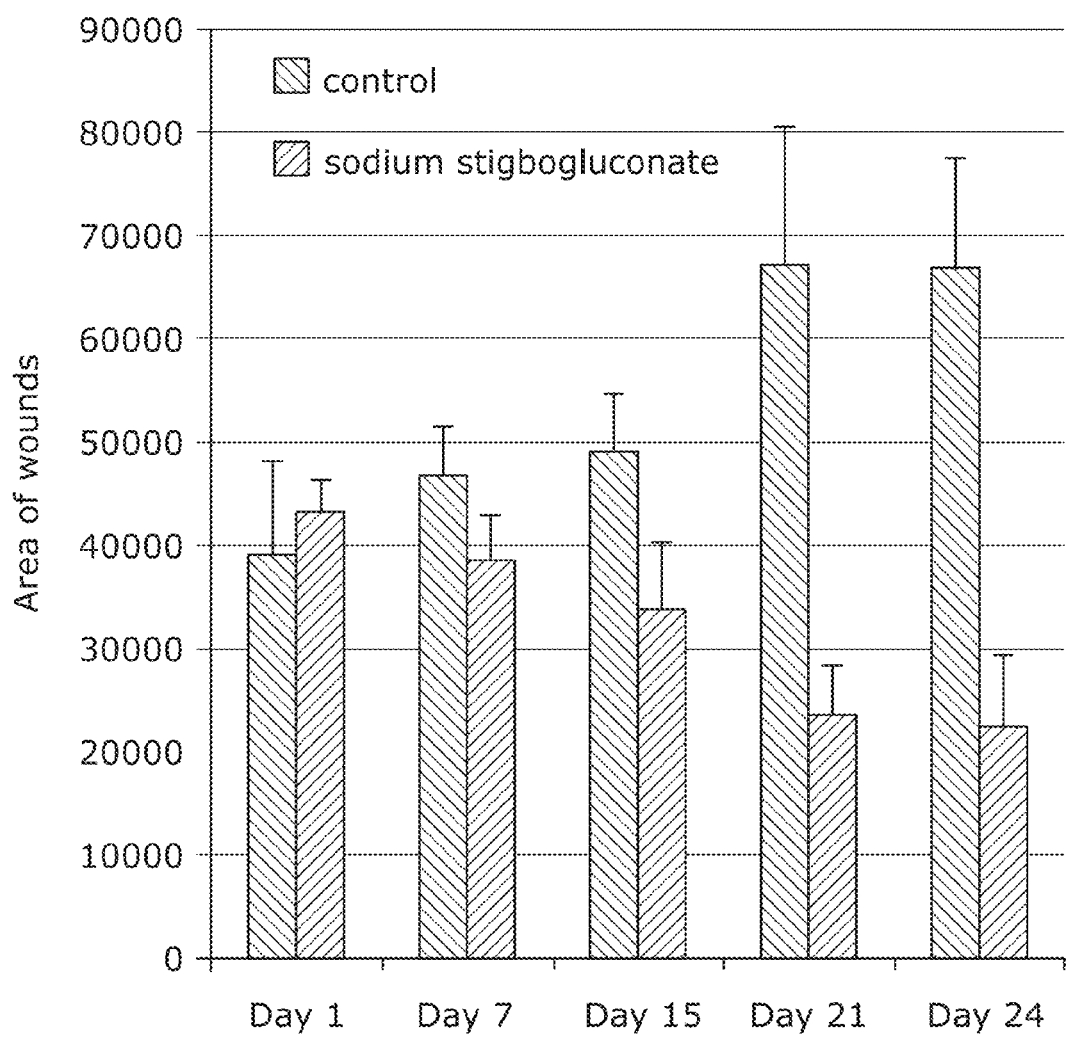
FIG. 11. Shows the effect of systemic administration of sodium stibogluconate, via the I.P. route, on the rate of wound healing.
Figure 12:
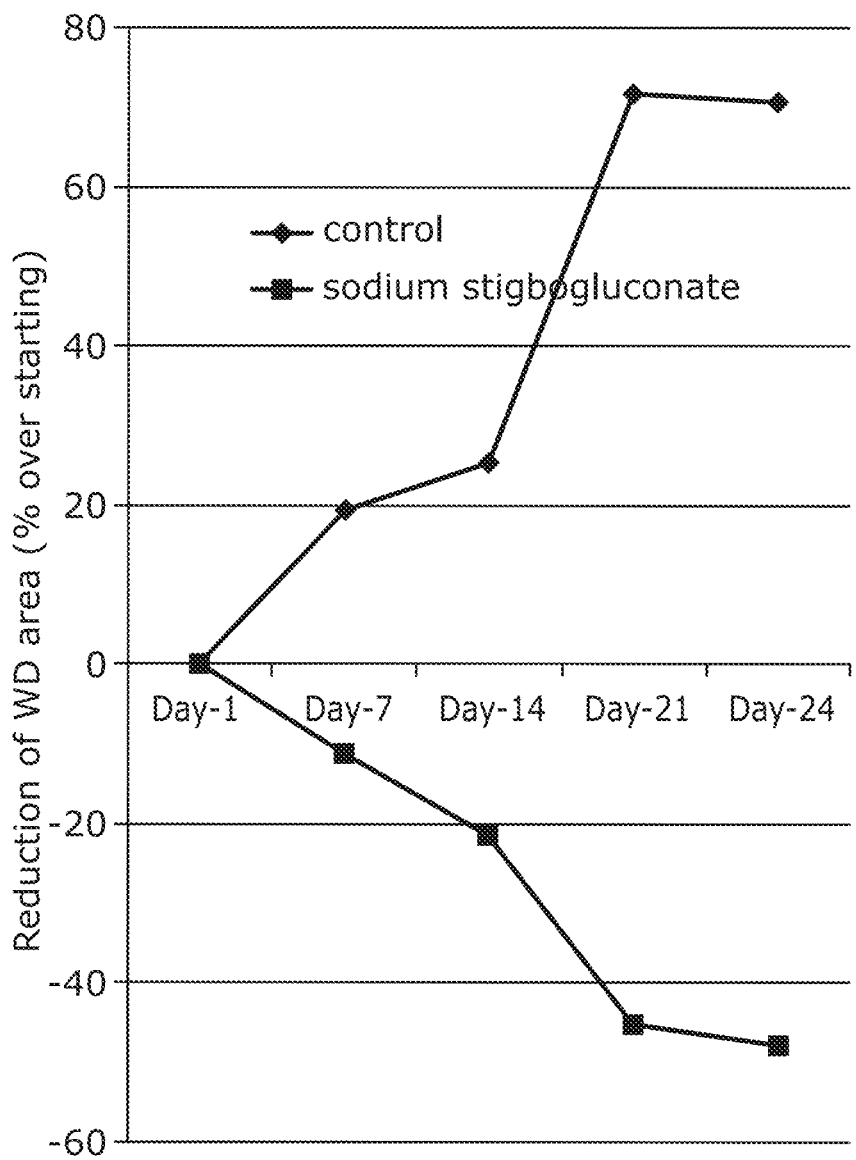
FIG. 12 Shows effects of stibogluconate on wound healing in the db/sb model. The compound was given topically every other day.

We have also tested the concentration related effect of PENTOSTAM™ (GlaxoSmithKline), a commercially available form of stibogluconate, on the migration of the cells, FIG. 10.

Stibogluconate was Well Tolerated In Vivo

The first tolerance test was conducted the CD-1 athymic (Charles River Laboratories). Briefly, CD-1 of 4-6 weeks old, 20 g in weight, were housed in filter topped cages. Sodium stibogluconate was injected, via the intraperitoneal route, on a daily basis. The compound was given at 100 final concentration (equivalent to 10 mg/kg body weight) in 100 ul in volume. CD-1 were observed daily, weighed twice weekly. An additional tolerance and efficacy test was carried out using the db/db strain.

Stibogluconate Accelerates Wound Healing In Vivo.

Formulation of the Compounds.

Figure 4:
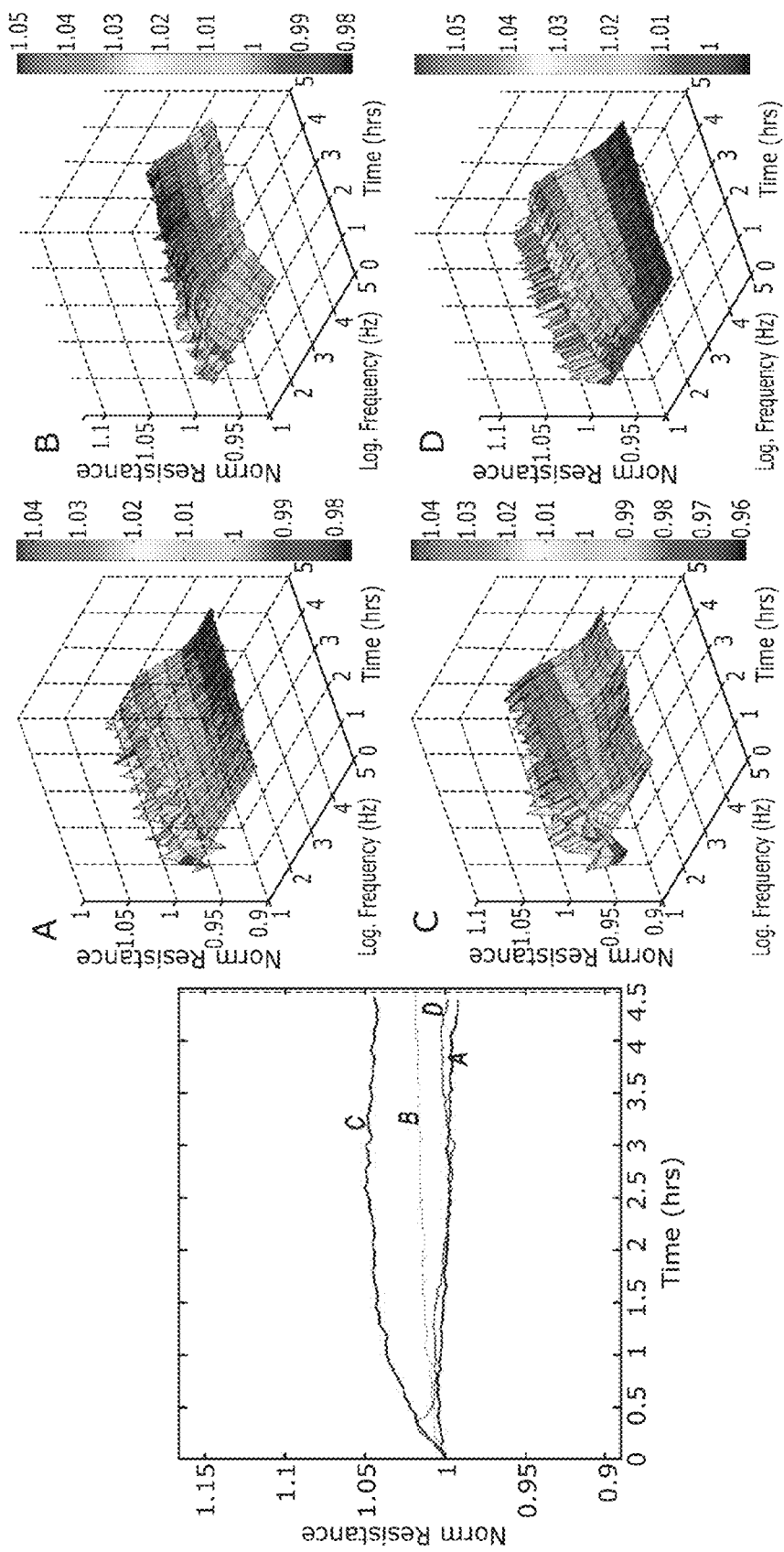
FIG. 4. Shows effects of knocking down PTPRK in endothelial cells on cellular migration s and their response to PTPRK inhibitor, stibogluconate. Left: traces of cells response in ECIS assays. Right: A: HECV WT, B: HECV/PTPRKrib; C: HECV wt plus stibogluconate; and D: cHECV/PTPRKrib plus stibogluconate. Cell were wounded at 6 v for 30 seconds and traced immediately after wounding.

1. For systemic application, Sodium stibogluconate was dissolved in BSS and diluted in the same for the required concentration. The solutions were prepared that each 100 ul contained the correct amount of compounds and was aliquatted and stored as such at $-20°$ C. until used. The compound was injected every other day by the IP route.
2. For topical application, we used two carrier gels that are currently used in wound care, namely Bactroban and Aquagel. From the concentrated master stock of Sodium stibogluconate, 100 ul of the stock solution was mixed with 2 grams of the respective gels, followed by low speed homogenisation using a hand held homogeniser, for 2 minutes. The newly formulated gels which showed no signed of changes of the strength and consistency, were stored at $4°$ C. until use. For use, small amount (150 ul) of the gel was applied to the wound area and gently rubbed in using fingers.
3. Sodium stibogluconate was well tolerated
   We have delivered the compounds systemically every other day, for a two week period in db/db. Throughout the study, we did not observe any side effects. There was no weight loss in any of the groups.
4. Sodium stibogluconate increased the rate of wound healing without producing any side effects.
   Sodium stibogluconate was given systemically, at 100 uM. After one week, wounds in the treated were smaller than the control group as shown in FIG. 1 (p=0.0927 vs control).
   However, topical application of Sodium stibogluconate showed no significant effect after one week, both in Bactroban and in Aquagel (FIGS. 2A-2B and 3).

In Vivo Test on the Dosing Effect and Exploration of the Optimal Way of Applying the Stibogluconate Using the same db/db mice, we further tested the possible dose response by applying stibogluconate at 2 mg/ml. 20 mg/ml and 100 mg/ml, using topical applications. At the same time, we tested two treatment methods: applying the agent on a weekly basis or twice weekly basis. We determined the size of the wound on a weekly basis. It was clear that both weekly and twice weekly application resulted in a rapid rate of wound healing. It was also clear that the therapeutic effects of stibogluconate is dependent on the dosage, in that the highest concentration used, namely 100 mg/ml appear to be most effective of all the concentrations using in the present study. Using a Two-way ANOVA (Holm-Sidak model), it was shown that in both treatment regimes, there was a highly significant difference between the treatment group and control group, p=0.013, 0.10 and 0.009, control vs 2 mg/ml, 20 mg/ml and 100 mg respectively, for the twice weekly treatment, and p=0.05, 0.013, 0.009 for the weekly treatment group.

Using Spearman correlation coefficient, we have found that after two weeks treatment, the size of the wounds was significantly correlated with the concentration (p=0.049, r=−0.950).

Figure 17:
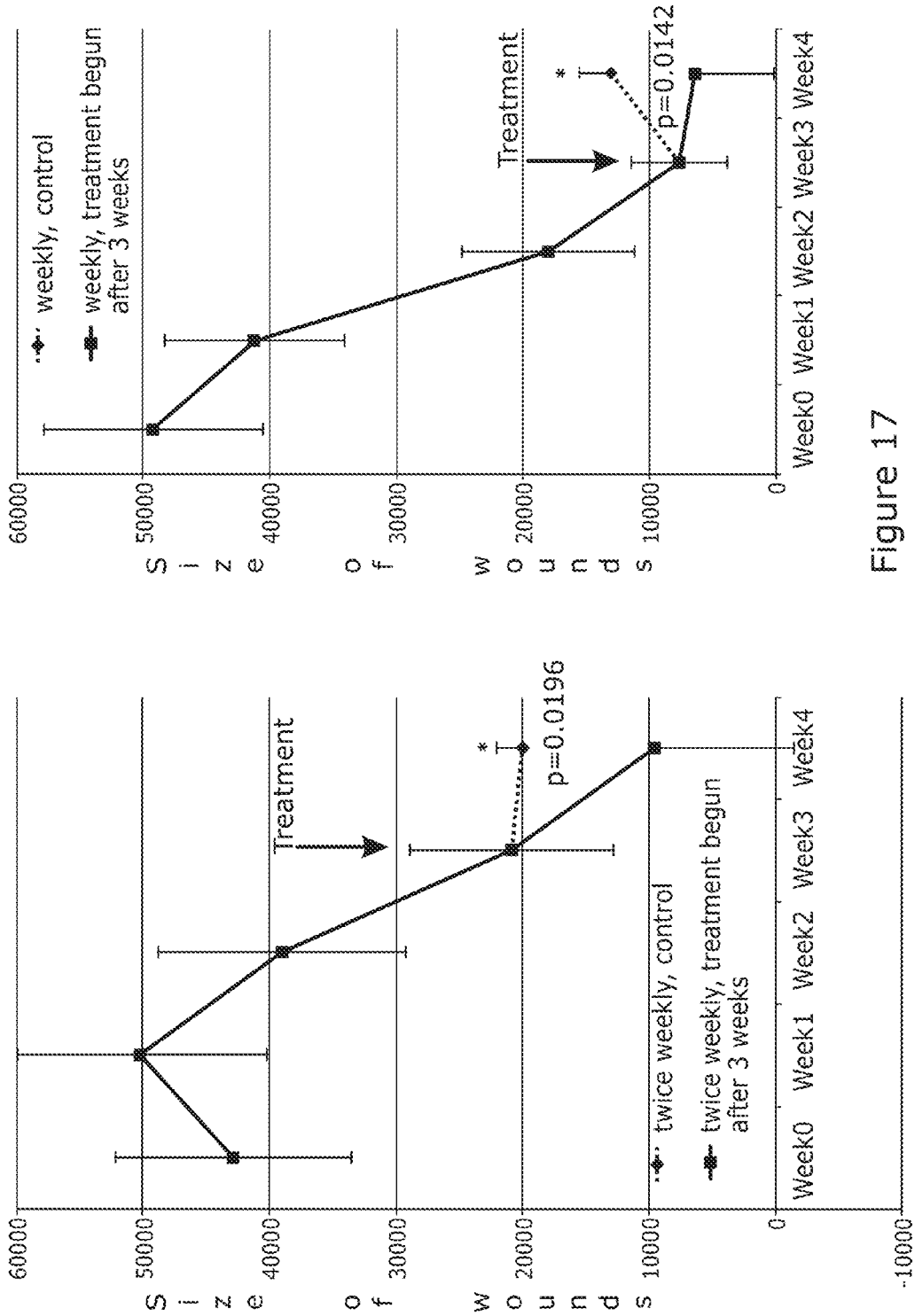
FIG. 17 shows the effect of removing treatment between the third and fourth week in either a weekly dosage regimen or a twice weekly dosage regimen; and Table 1. shows the primers and oligonulceotides used for the Construction and verification of ant-human PTPRK ribozyme transgenes described herein.

Further, we have also shown that interrupting treatment, in either a weekly or twice weekly dosing regimen, prior to complete healing had a significant effect on the healing process, resulting a noticeable reduction in wound closure (FIG. 17).

Summary

The main findings of the present study can be summarised as follows:

In wound tissue PTPRK is an important regulator of the migration of keratinocytes. PTPRK responds to a PTPRK inhibitor, stibogluconate, by way of increasing the adhesion and in particular migration of keratinocytes and also the migration of vascular endothelial cells. Moreover, Stibugluconate has a concentration dependent effect on the migration of keratinocytes. In vivo, both topical and systemic administration of stibogluconate increased the rate of wound healing, without noticeable side effects. The effect of stibogluconate on wound healing in vivo appears to be dose dependent. Both weekly and twice weekly administration of stibogluconate significantly increased the rate of wound healing, although twice weekly appears to be marginally more effective. Interrupting the treatment regimen adversely affects the healing process.

These findings collectively show that PTPRK is critical in controlling the migration and healing of wounds. Thus, both in vitro and clinical data point to PTPRK being an important therapeutic target in wounds.

TABLE 1

Primer and oligo sequences used in the present study.

| Primer names | Sense primers | Anti-sense primers |
|---|---|---|
| PTPRK pair F11/R11 | Aattacaattgatggggaga (SEQ ID NO: 10) | Ccactttccacctgaagta (SEQ ID NO: 11) |
| PTPRK pair ZF11/ZR11 | Aattacaattgatggggaga (SEQ ID NO: 10) | Actgaacctgaccgtacacatattgtgtgacgatgaaagc (SEQ ID NO: 12) |
| PTPRK pair F12/R12 | Gcgagtcaagttatcaaacc (SEQ ID NO: 13) | Tgtagctgtccataagagca (SEQ ID NO: 14) |
| PTPRK pair ZF12/ZR12 | Gcgagtcaagttatcaaacc (SEQ ID NO: 15) | Actgaacctgaccgtacacactctttcagccatgtctagc (SEQ ID NO: 16) |
| Anti-PTPRK transgene-1 | Ctgcagagtgagttacacagcctgatgagtccgtgagga (SEQ ID NO: 1) | Actagtgacaaaaactg accaggatttgtAtttcgtcctcacggact (SEQ ID NO: 2) |
| Anti-PTPRK transgene-2 | Ctgcaggatgataggaccatcgccaatctgatgagtccgtgagga (SEQ ID NO: 3) | ActagtgatccaactaaatgccaactcgAtttcgtcctcacggact (SEQ ID NO: 4) |
| Anti-PTPRK transgene-3 | Ctgcagtttgctcttttttacaattaatatctgatgagtccgtgagga (SEQ ID NO: 5) | ActagttcatcctccttctcctagttGtttcgtctcacggact (SEQ ID NO: 6) |
| T7F and BGHR | Taatacgactcactataggg (SEQ ID NO: 17) | Tagaaggcacagtcgagg (SEQ ID NO: 18) |
| RBTPF and RBBMR | Ctgatgagtccgtgaggacgaa (SEQ ID NO: 19) | Ttcgtcctcacggactcatcag (SEQ ID NO: 20) |

What is claimed:

1. A method for treating a mammalian non-parasitic wound, comprising administering to said wound a therapeutic comprising an inhibitor of PTPRK protein activity, wherein said inhibitor is Stibogluconate or a salt thereof.

2. The method according to claim 1, wherein said non-parasitic wound is a chronic wound.

3. The method according to claim 2, wherein said chronic wound is selected from the group consisting of venous ulcers, diabetic ulcers, and pressure ulcers.

4. The method according to claim 1, wherein said non-parasitic wound is a human wound.

5. The method according to claim 1, including formulating said therapeutic for topical application.

6. The method according to claim 1, including formulating said therapeutic for application to a dressing or impregnated in a dressing.

7. The method according to claim 1, including formulating said therapeutic with a pharmaceutically or veterinarily acceptable carrier or vehicle.

8. The method according to claim 5, wherein said topical formulation comprises a hydrogel.

9. A method for treating a chronic human non-parasitic wound, comprising administering a topical formulation comprising Stibogluconate or a salt thereof.

10. The method according to claim 9, including formulating said topical formulation for application to a dressing or impregnated in a dressing.

11. The method according to claim 10, including formulating said topical formulation with a pharmaceutically or veterinarily acceptable carrier or vehicle.

* * * * *

SEQUENCE LISTING

<160> NUMBER OF SEQ ID NOS: 22

<210> SEQ ID NO 1
<211> LENGTH: 39
<212> TYPE: DNA
<213> ORGANISM: Homo sapiens

<400> SEQUENCE: 1
ctgcagagtg agttacacag cctgatgagt ccgtgagga         39

<210> SEQ ID NO 2
<211> LENGTH: 47
<212> TYPE: DNA
<213> ORGANISM: Homo sapiens

<400> SEQUENCE: 2
actagtgaca aaaactgacc aggatttgta tttcgtcctc acggact         47

```
<210> SEQ ID NO 3
<211> LENGTH: 45
<212> TYPE: DNA
<213> ORGANISM: Homo sapiens

<400> SEQUENCE: 3
ctgcaggatg ataggaccat cgccaatctg atgagtccgt gagga            45

<210> SEQ ID NO 4
<211> LENGTH: 46
<212> TYPE: DNA
<213> ORGANISM: Homo sapiens

<400> SEQUENCE: 4
actagtgatc caactaaatg ccaactcgat tcgtcctca cggact            46

<210> SEQ ID NO 5
<211> LENGTH: 48
<212> TYPE: DNA
<213> ORGANISM: Homo sapiens

<400> SEQUENCE: 5
ctgcagtttg ctcttttta caattaatat ctgatgagtc cgtgagga           48

<210> SEQ ID NO 6
<211> LENGTH: 44
<212> TYPE: DNA
<213> ORGANISM: Homo sapiens

<400> SEQUENCE: 6
actagttcat cctccttctc ctagttgttt cgtcctcacg gact              44

<210> SEQ ID NO 7
<211> LENGTH: 74
<212> TYPE: DNA
<213> ORGANISM: Homo sapiens

<400> SEQUENCE: 7
ctgcagagtg agttacacag cctgatgagt ccgtgaggac gaaatacaaa tcctggtcag   60
tttttgttac tagt                                              74

<210> SEQ ID NO 8
<211> LENGTH: 79
<212> TYPE: DNA
<213> ORGANISM: Homo sapiens

<400> SEQUENCE: 8
ctgcaggatg ataggaccat cgccaatctg atgagtccgt gaggacgaaa tcgagttggc   60
atttagttgg atcactagt                                         79

<210> SEQ ID NO 9
<211> LENGTH: 80
<212> TYPE: DNA
<213> ORGANISM: Homo sapiens

<400> SEQUENCE: 9
ctgcagtttg ctcttttta caattaatat ctgatgagtc cgtgaggacg aaacaactag   60
gagaaggagg atgaactagt                                        80
```

```
<210> SEQ ID NO 10
<211> LENGTH: 20
<212> TYPE: DNA
<213> ORGANISM: Homo sapiens

<400> SEQUENCE: 10
aattacaatt gatggggaga                                                    20

<210> SEQ ID NO 11
<211> LENGTH: 20
<212> TYPE: DNA
<213> ORGANISM: Homo sapiens

<400> SEQUENCE: 11 ccactttcc acctgaagta                                                     20

<210> SEQ ID NO 12
<211> LENGTH: 40
<212> TYPE: DNA
<213> ORGANISM: Homo sapiens

<400> SEQUENCE: 12
actgaacctg accgtacaca tattgtgtga cgatgaaagc                              40

<210> SEQ ID NO 13
<211> LENGTH: 20
<212> TYPE: DNA
<213> ORGANISM: Homo sapiens

<400> SEQUENCE: 13
gcgagtcaag ttatcaaacc                                                    20

<210> SEQ ID NO 14
<211> LENGTH: 20
<212> TYPE: DNA
<213> ORGANISM: Homo sapiens

<400> SEQUENCE: 14
tgtagctgtc cataagagca                                                    20

<210> SEQ ID NO 15
<211> LENGTH: 20
<212> TYPE: DNA
<213> ORGANISM: Homo sapiens

<400> SEQUENCE: 15
gcgagtcaag ttatcaaacc                                                    20

<210> SEQ ID NO 16
<211> LENGTH: 40
<212> TYPE: DNA
<213> ORGANISM: Homo sapiens

<400> SEQUENCE: 16
actgaacctg accgtacaca ctctttcagc catgtctagc                              40

<210> SEQ ID NO 17
<211> LENGTH: 20
<212> TYPE: DNA
<213> ORGANISM: Homo sapiens

<400> SEQUENCE: 17
taatacgact cactataggg                                                    20
```

<210> SEQ ID NO 18
<211> LENGTH: 18
<212> TYPE: DNA
<213> ORGANISM: Homo sapiens

<400> SEQUENCE: 18
tagaaggcac agtcgagg                                                    18

<210> SEQ ID NO 19
<211> LENGTH: 22
<212> TYPE: DNA
<213> ORGANISM: Homo sapiens

<400> SEQUENCE: 19
ctgatgagtc cgtgaggacg aa                                               22

<210> SEQ ID NO 20
<211> LENGTH: 22
<212> TYPE: DNA
<213> ORGANISM: Homo sapiens

<400> SEQUENCE: 20
ttcgtcctca cggactcatc ag                                               22

<210> SEQ ID NO 21
<211> LENGTH: 4320
<212> TYPE: DNA
<213> ORGANISM: Homo sapiens

<400> SEQUENCE: 21
atggatacga ctgcggcggc ggcgctgcct gcttttgtgg cgctcttgct cctctctcct      60
tggcctctcc tgggatcggc ccaaggccag ttctccgcag gtggctgtac ttttgatgat     120
ggtccagggg cctgtgatta ccaccaggat ctgtatgatg actttgaatg ggtgcatgtt     180
agtgctcaag agcctcatta tctaccaccc gagatgcccc aaggttccta tatgatagtg     240
gactcttcag atcacgaccc tggagaaaaa gccagacttc agctgcctac aatgaaggag     300
aacgacactc actgcattga tttcagttac ctattatata gccagaaagg actgaatcct     360
ggcactttga acatattagt tagggtgaat aaaggacctc ttgccaatcc aatttggaat     420
gtgactggat tcacgggtag agattggctt cgggctgagc tagcagtgag ctccttttgg     480
cccaatgaat atcaggtaat atttgaagct gaagtctcag gagggagaag tggttatatt     540
gccattgatg acatccaagt actgagttat ccttgtgata aatctcctca tttcctccgt     600
ctaggggatg tagaggtgaa tgcagggcaa aacgctacat ttcagtgcat tgccacaggg     660
agagatgctg tgcataacaa gttatggctc cagagacgaa atggagaaga tacccagta      720 gcccagacta agaacatcaa tcatagaagg tttgccgctt ccttcagatt gcaagaagtg     780
acaaaaactg accaggattt gtatcgctgt gtaactcagt cagaacgagg ttccggtgtg     840
tccaattttg ctcaacttat tgtgagagaa ccgccaagac ccattgctcc tcctcagctt     900
cttggtgttg ggcctacata tttgctgatc caactaaatg ccaactcgat cattggcgat     960
ggtcctatca tcctgaaaga agtagagtac cgaatgacta caggatcctg acagaaaacc    1020
catgcagtca atgctccaac ttacaaatta tggcatttag atccagatac cgaatatgag    1080
atccgagttc tacttacaag acctggtgaa ggtggaacgg ggctcccagg acctccacta    1140
atcaccagaa caaaatgtgc agaacctatg agaaccccaa agacattaaa gattgctgaa    1200
atacaggcaa gacggattgc tgtggactgg gaatccttgg gttacaacat tacgcgttgc    1260

```
cacactttta atgtcactat ctgctaccat tacttccgtg gtcacaacga gagcaaggca  1320
gactgtttgg acatggaccc caaagcccct cagcatgttg tgaaccatct gccaccttat  1380
acaaatgtca gcctcaagat gatcctaacc aatccagagg gaaggaagga gagtgaagag  1440
acaattattc aaactgatga agatgtgcct ggtcccgtac cagtaaaatc tcttcaagga  1500
acatcctttg aaaataagat cttcttgaac tggaaagaac ctttggatcc aaatggaatc  1560
atcactcaat atgagatcag ctatagcagt ataagatcat ttgatcctgc agtcccagtg  1620
gctggacctc cccagactgt atcaaattta tggaacagta cacaccatgt ctttatgcat  1680
ctccaccctg gaaccacgta ccagtttttc ataagagcca gcacggtcaa aggctttggt  1740
ccagccacag ccatcaatgt caccaccaat atctcagctc caactttacc tgactatgaa  1800
ggagttgatg cctctctcaa tgaaactgcc accacaataa ctgtattgtt gagaccagca  1860
caagccaaag gtgctcctat cagtgcttat cagattgttg tggaagaact gcacccacac  1920
cgaaccaaga gagaagccgg agccatggaa tgctaccagg ttcctgtcac ataccaaaat  1980
gccatgagtg ggggtgcacc gtattacttt gctgcagaac taccccgggg aaacctacct  2040
gagcctgccc cgttcactgt gggtgacaat cggacctacc aaggcttttg gaaccctcct  2100
ttggctccgc gcaaaggata caacatctat ttccaggcga tgagcagtgt ggagaaggaa  2160
actaaaaccc agtgcgtacg cattgctaca aaagcagcaa cagaagaacc agaagtgatc  2220
ccagatcccg ccaagcagac agacagagtg gtgaaaatag caggaattag tgctggaatt  2280
ttggtgttca tcctccttct cctagttgtc atattaattg taaaaaagag caaacttgct  2340
aaaaaacgca aagatgccat ggggaatacc cggcaggaga tgactcacat ggtgaatgca  2400
atggatcgaa gttatgctga tcagagcact ctgcatgcag aagatcctct ttccatcacc  2460
ttcatggacc aacataactt tagtccaaga tatgagaacc acagtgctac agcagagtcc  2520
agtcgccttc tagacgtacc tcgctacctc tgtgagggga cggaatcccc ttaccagaca  2580
ggacagctgc atccagccat cagggtagct gatttactgc agcacattaa tctcatgaag  2640
acatcagaca gctatgggtt caaagaggaa tatgagagct ttttgaagg acagtcagca  2700
tcttgggatg tagctaaaaa agatcaaaat agagcaaaaa accgatatgg aaacattata  2760
gcatatgatc actccagagt gattttgcaa cccgtagagg atgatcctc ctcagattat  2820
attaatgcca actatattga tggctaccag agaccaagtc attacattgc aacccaaggt  2880
cccgttcatg aaacagtgta tgatttctgg aggatgattt ggcaagaaca atctgcttgc  2940
attgtgatgg ttacaaattt agttgaggtt ggccgggtta aatgctataa atattggcct  3000
gatgatactg aagtttatgg tgacttcaaa gtaacgtgtg tagaaatgga accacttgct  3060
gaatatgtag ttaggacatt caccctggaa aggaggggt acaatgaaat ccgtgaagtt  3120
aaacagttcc atttcacggg ctggcctgac catggagtgc cctaccatgc tacagggctg  3180
ctttcctta tccggcgagt caagttatca aaccctccca gtgctggccc catcgttgta  3240
cattgcagtg ctggtgctgg acgaactggc tgctacattg tgattgacat catgctagac  3300
atggctgaaa gagagggtgt tgttgatatt tacaattgtg tcaaagcctt aagatctcgg  3360
cgtattaata tggtccagac agaggaacag tacatttta ttcatgatgc cattttagaa  3420
gcctgcttat gtggagaaac tgccatacct gtctgtgaat ttaaagctgc atattttgat  3480
atgattagaa tagactccca gactaactct tcacatctca aggatgaatt tcagactctg  3540
aattcagtca cccctcgact acaagctgaa gactgcagta tagcgtgcct gccaaggaac  3600
catgacaaga accgtttcat ggacatgctg ccacctgaca gatgtctgcc ttttttaatt  3660
```

-continued

| | |
|---|---|
| acaattgatg gggagagcag taactacatc aatgctgctc ttatggacag ctacaggcaa | 3720 |
| ccagctgctt tcatcgtcac acaatacccct ctgccaaaca ctgtaaaaga cttctggaga | 3780 |
| ttagtgtatg attatggctg tacctccatt gtgatgttaa acgaagtcga cttgtcccag | 3840 |
| ggctgccctc agtactggcc agaggaaggg atgctacgat atggccccat ccaagtggaa | 3900 |
| tgtatgtctt gttcaatgga ctgtgatgtg atcaaccgga tttttaggat atgcaatcta | 3960 |
| acaagaccac aggaaggtta tctgatggtg caacagtttc agtacctagg atgggcttct | 4020 |
| catcgagaag tgcctggatc caaaaggtca ttcttgaaac tgatacttca ggtggaaaag | 4080 |
| tggcaggagg aatgcgagga aggggaaggc cggacgatta tccactgcct aaatggtggc | 4140 |
| gggcgaagtg gcatgttctg tgctataggc atcgttgttg aaatggtgaa acggcaaaat | 4200 |
| gttgtcgatg ttttccatgc agtaaagaca ctgaggaaca gcaagccaaa catggtggaa | 4260 |
| gccccggagc aataccgttt ctgctatgat gtagctttgg agtacctgga atcatcttag | 4320 |

<210> SEQ ID NO 22
<211> LENGTH: 1428
<212> TYPE: PRT
<213> ORGANISM: Homo sapiens

<400> SEQUENCE: 22

```
Met Asp Thr Thr Ala Ala Ala Leu Pro Ala Phe Val Ala Leu Leu
1               5                   10                  15

Leu Leu Ser Pro Trp Pro Leu Leu Gly Ser Ala Gln Gly Gln Phe Ser
            20                  25                  30

Ala Gly Gly Cys Thr Phe Asp Asp Gly Pro Gly Ala Cys Asp Tyr His
        35                  40                  45

Gln Asp Leu Tyr Asp Asp Phe Glu Trp Val His Val Ser Ala Gln Glu
    50                  55                  60

Pro His Tyr Leu Pro Pro Glu Met Pro Gln Gly Ser Tyr Met Ile Val
65                  70                  75                  80

Asp Ser Ser Asp His Asp Pro Gly Glu Lys Ala Arg Leu Gln Leu Pro
                85                  90                  95

Thr Met Lys Glu Asn Asp Thr His Cys Ile Asp Phe Ser Tyr Leu Leu
            100                 105                 110

Tyr Ser Gln Lys Gly Leu Asn Pro Gly Thr Leu Asn Ile Leu Val Val
        115                 120                 125

Asn Lys Gly Pro Leu Ala Asn Pro Ile Trp Asn Val Thr Gly Phe Thr
    130                 135                 140

Gly Arg Asp Trp Leu Arg Ala Glu Leu Ala Val Ser Ser Phe Trp Pro
145                 150                 155                 160

Asn Glu Tyr Gln Val Ile Phe Glu Ala Glu Val Ser Gly Gly Arg Ser
                165                 170                 175

Gly Tyr Ile Ala Ile Asp Asp Ile Gln Val Leu Ser Tyr Pro Cys Asp
            180                 185                 190

Lys Ser Pro His Phe Leu Arg Leu Gly Asp Val Glu Val Asn Ala Gly
        195                 200                 205

Gln Asn Ala Thr Phe Gln Cys Ile Ala Thr Gly Arg Asp Ala Val His
    210                 215                 220

Asn Lys Leu Trp Leu Gln Arg Arg Asn Gly Glu Asp Ile Pro Val Ala
225                 230                 235                 240

Gln Thr Lys Asn Ile Asn His Arg Arg Phe Ala Ala Ser Phe Leu Gln
                245                 250                 255
```

-continued

```
Glu Val Thr Lys Thr Asp Gln Asp Leu Tyr Arg Cys Val Thr Gln Ser
            260                 265                 270

Glu Arg Gly Ser Gly Val Ser Asn Phe Ala Gln Leu Ile Val Arg Glu
        275                 280                 285

Pro Pro Arg Pro Ile Ala Pro Pro Gln Leu Leu Gly Val Gly Pro Thr
        290                 295                 300

Tyr Leu Leu Ile Gln Leu Asn Ala Asn Ser Ile Ile Gly Asp Gly Pro
305                 310                 315                 320

Ile Ile Leu Lys Glu Val Glu Tyr Arg Met Thr Ser Gly Ser Trp Thr
                325                 330                 335

Glu Thr His Ala Val Asn Ala Pro Thr Tyr Lys Leu Trp His Leu Asp
            340                 345                 350

Pro Asp Thr Glu Tyr Glu Ile Arg Val Leu Leu Thr Arg Pro Gly Glu
        355                 360                 365

Gly Gly Thr Gly Leu Pro Gly Pro Pro Leu Ile Thr Arg Lys Cys Ala
        370                 375                 380

Glu Pro Met Arg Thr Pro Lys Thr Leu Lys Ile Ala Glu Ile Gln Ala
385                 390                 395                 400

Arg Arg Ile Ala Val Asp Trp Glu Ser Leu Gly Tyr Asn Ile Thr Arg
                405                 410                 415

Cys His Thr Phe Asn Val Thr Ile Cys Tyr His Tyr Phe Arg Gly His
            420                 425                 430

Asn Glu Ser Lys Ala Asp Cys Leu Asp Met Asp Pro Lys Ala Pro Gln
        435                 440                 445

His Val Val Asn His Leu Pro Pro Tyr Thr Asn Val Ser Leu Lys Met
        450                 455                 460

Ile Leu Thr Asn Pro Glu Gly Arg Lys Glu Ser Glu Glu Thr Ile Ile
465                 470                 475                 480

Gln Thr Asp Glu Asp Val Pro Gly Pro Val Pro Val Lys Ser Leu Gln
                485                 490                 495

Gly Thr Ser Phe Glu Asn Lys Ile Phe Leu Asn Trp Glu Pro Leu Asp
            500                 505                 510

Pro Asn Gly Ile Ile Thr Gln Tyr Glu Ile Ser Tyr Ser Ser Ile Arg
        515                 520                 525

Ser Phe Asp Pro Ala Val Pro Val Ala Gly Pro Pro Gln Thr Val Ser
        530                 535                 540

Asn Leu Trp Asn Ser Thr His His Val Phe Met His Leu His Pro Gly
545                 550                 555                 560

Thr Thr Tyr Gln Phe Phe Ile Arg Ala Ser Thr Val Lys Gly Phe Gly
                565                 570                 575

Pro Ala Thr Ala Ile Asn Val Thr Thr Asn Ile Ser Ala Pro Thr Leu
            580                 585                 590

Pro Asp Tyr Glu Gly Val Asp Ala Ser Leu Asn Glu Thr Ala Thr Thr
        595                 600                 605

Ile Thr Val Leu Leu Arg Pro Ala Gln Ala Lys Gly Ala Pro Ile Ser
        610                 615                 620

Ala Tyr Gln Ile Val Val Glu Glu Leu His Pro Arg Thr Lys Arg Glu
625                 630                 635                 640

Ala Gly Ala Met Glu Cys Tyr Gln Val Pro Val Thr Tyr Gln Asn Ala
                645                 650                 655

Met Ser Gly Gly Ala Pro Tyr Tyr Phe Ala Ala Glu Leu Pro Pro Gly
            660                 665                 670
```

-continued

Asn Leu Pro Glu Pro Ala Pro Phe Thr Val Gly Asp Asn Arg Thr Tyr
675                 680                 685

Gln Gly Phe Trp Asn Pro Pro Leu Ala Pro Arg Lys Gly Tyr Asn Ile
690                 695                 700

Tyr Phe Gln Ala Met Ser Ser Val Glu Lys Thr Lys Thr Gln Cys
705                 710                 715                 720

Val Arg Ile Ala Thr Lys Ala Ala Thr Glu Glu Pro Glu Val Ile Pro
                725                 730                 735

Asp Pro Ala Lys Gln Thr Asp Arg Val Lys Ile Ala Gly Ile Ser
                740                 745                 750

Ala Gly Ile Leu Val Phe Ile Leu Leu Val Ile Leu Ile Val
                755                 760                 765

Lys Lys Ser Lys Leu Ala Lys Lys Arg Lys Asp Ala Met Gly Asn Thr
770                 775                 780

Arg Gln Glu Met Thr His Met Val Asn Ala Met Asp Arg Ser Tyr Ala
785                 790                 795                 800

Asp Gln Ser Thr Leu His Ala Glu Asp Pro Leu Ser Ile Thr Phe Met
                805                 810                 815

Asp Gln His Asn Phe Ser Pro Arg Tyr Glu Asn His Ser Ala Thr Ala
                820                 825                 830

Glu Ser Ser Arg Leu Leu Asp Val Pro Arg Tyr Leu Cys Glu Gly Thr
                835                 840                 845

Glu Ser Pro Tyr Gln Thr Gly Gln Leu His Pro Ala Ile Arg Val Ala
                850                 855                 860

Asp Leu Leu Gln His Ile Asn Leu Met Lys Thr Ser Asp Ser Tyr Gly
865                 870                 875                 880

Phe Lys Glu Glu Tyr Glu Ser Phe Phe Gly Gln Ser Ala Ser Trp Asp
                885                 890                 895

Val Ala Lys Lys Asp Gln Asn Arg Ala Lys Asn Arg Tyr Gly Asn Ile
                900                 905                 910

Ile Ala Tyr Asp His Ser Arg Val Ile Leu Gln Pro Val Glu Asp Asp
                915                 920                 925

Pro Ser Ser Asp Tyr Ile Asn Ala Asn Tyr Ile Asp Gly Tyr Gln Arg
930                 935                 940

Pro Ser His Tyr Ile Ala Thr Gln Gly Pro Val His Glu Thr Val Tyr
945                 950                 955                 960

Asp Phe Trp Arg Met Ile Trp Gln Glu Gln Ser Ala Cys Ile Val Met
                965                 970                 975

Val Thr Asn Leu Val Glu Val Gly Arg Val Lys Cys Tyr Lys Tyr Trp
                980                 985                 990

Pro Asp Asp Thr Glu Val Tyr Gly Asp Phe Lys Val Thr Cys Val Glu
                995                 1000                 1005

Met Glu Pro Leu Ala Glu Tyr Val Arg Thr Phe Thr Leu Glu Arg
1010                 1015                 1020

Arg Gly Tyr Asn Glu Ile Arg Glu Val Lys Gln Phe His Phe Thr
1025                 1030                 1035

Gly Trp Pro Asp His Gly Val Pro Tyr His Ala Thr Gly Leu Leu
1040                 1045                 1050

Ser Phe Ile Arg Arg Val Lys Leu Ser Asn Pro Pro Ser Ala Gly
1055                 1060                 1065

Pro Ile Val Val His Cys Ser Ala Gly Ala Gly Arg Thr Gly Cys
1070                 1075                 1080

-continued

| | | | | | | | | | | | |
|---|---|---|---|---|---|---|---|---|---|---|---|
| Tyr | Ile 1085 | Val | Ile | Asp | Ile 1090 | Met | Leu | Asp | Met | Ala 1095 | Glu | Arg | Glu | Gly |
| Val | Val 1100 | Asp | Ile | Tyr | Asn 1105 | Cys | Val | Lys | Ala | Leu 1110 | Arg | Ser | Arg | Arg |
| Ile | Asn 1115 | Met | Val | Gln | Thr 1120 | Glu | Glu | Gln | Tyr | Ile 1125 | Phe | Ile | His | Asp |
| Ala | Ile 1130 | Leu | Glu | Ala | Cys 1135 | Leu | Cys | Gly | Glu | Thr 1140 | Ala | Ile | Pro | Val |
| Glu | Phe 1145 | Lys | Ala | Ala | Tyr 1150 | Phe | Asp | Met | Ile | Arg 1155 | Ile | Asp | Ser | Gln |
| Thr | Asn 1160 | Ser | Ser | His | Leu 1165 | Lys | Asp | Glu | Phe | Gln 1170 | Thr | Leu | Asn | Ser |
| Val | Thr 1175 | Pro | Arg | Leu | Gln 1180 | Ala | Glu | Asp | Cys | Ser 1185 | Ile | Ala | Cys | Leu |
| Pro | Arg 1190 | Asn | His | Asp | Lys 1195 | Asn | Arg | Phe | Met | Asp 1200 | Met | Leu | Pro | Pro |
| Asp | Arg 1205 | Cys | Leu | Pro | Phe 1210 | Leu | Ile | Thr | Ile | Asp 1215 | Gly | Glu | Ser | Ser |
| Asn | Tyr 1220 | Ile | Asn | Ala | Ala 1225 | Leu | Met | Asp | Ser | Tyr 1230 | Arg | Gln | Pro | Ala |
| Ala | Phe 1235 | Ile | Val | Thr | Gln 1240 | Tyr | Pro | Leu | Pro | Asn 1245 | Thr | Val | Lys | Asp |
| Phe | Trp 1250 | Arg | Leu | Val | Tyr 1255 | Asp | Tyr | Gly | Cys | Thr 1260 | Ser | Ile | Val | Met |
| Leu | Asn 1265 | Glu | Val | Asp | Leu 1270 | Ser | Gly | Cys | Pro | Gln 1275 | Tyr | Trp | Pro | Glu |
| Glu | Gly 1280 | Met | Leu | Arg | Tyr 1285 | Gly | Pro | Ile | Gln | Val 1290 | Glu | Cys | Met | Ser |
| Cys | Ser 1295 | Met | Asp | Cys | Asp 1300 | Val | Ile | Asn | Arg | Ile 1305 | Phe | Arg | Ile | Cys |
| Asn | Leu 1310 | Thr | Arg | Pro | Gln 1315 | Glu | Gly | Tyr | Leu | Met 1320 | Val | Gln | Gln | Phe |
| Gln | Tyr 1325 | Leu | Gly | Trp | Ala 1330 | Ser | His | Arg | Glu | Val 1335 | Pro | Gly | Ser | Lys |
| Arg | Ser 1340 | Phe | Leu | Lys | Leu 1345 | Ile | Leu | Gln | Val | Glu 1350 | Lys | Trp | Gln | Glu |
| Glu | Cys 1355 | Glu | Glu | Gly | Glu 1360 | Gly | Arg | Thr | Ile | Ile 1365 | His | Cys | Leu | Asn |
| Gly | Gly 1370 | Gly | Arg | Ser | Gly 1375 | Met | Phe | Cys | Ala | Ile 1380 | Gly | Ile | Val | Val |
| Glu | Met 1385 | Val | Lys | Arg | Gln 1390 | Asn | Val | Val | Asp | Val 1395 | Phe | His | Ala | Lys |
| Thr | Leu 1400 | Arg | Asn | Ser | Lys 1405 | Pro | Asn | Met | Val | Glu 1410 | Ala | Pro | Glu | Gln |
| Tyr | Arg 1415 | Phe | Cys | Tyr | Asp 1420 | Val | Ala | Leu | Glu | Tyr 1425 | Leu | Glu | Ser | Ser |